(12) United States Patent
Laposta et al.

(10) Patent No.: US 9,138,279 B2
(45) Date of Patent: Sep. 22, 2015

(54) FIXATION ASSEMBLY

(71) Applicant: DEPUY SYNTHES PRODUCTS, LLC, Raynham, MA (US)

(72) Inventors: Marie Laposta, West Chester, PA (US); Jared Schoenly, West Chester, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

(21) Appl. No.: 14/512,621

(22) Filed: Oct. 13, 2014

(65) Prior Publication Data
US 2015/0032115 A1 Jan. 29, 2015

Related U.S. Application Data

(63) Continuation of application No. 13/087,659, filed on Apr. 15, 2011, now Pat. No. 8,882,775.

(51) Int. Cl.
*A61B 17/88* (2006.01)
*A61F 2/46* (2006.01)
(Continued)

(52) U.S. Cl.
CPC ......... *A61B 17/8872* (2013.01); *A61B 17/8894* (2013.01); *A61F 2/4611* (2013.01); *A61B 17/7082* (2013.01); *A61B 2017/681* (2013.01); *A61F 2/30744* (2013.01); *A61F 2/30749* (2013.01); *A61F 2/30771* (2013.01); *A61F 2/30965* (2013.01); *A61F 2/442* (2013.01); *A61F 2/447* (2013.01); *A61F 2/4465* (2013.01); (Continued)

(58) Field of Classification Search
CPC ............ A61B 17/8872; A61B 2017/681

USPC ................... 606/86 R, 99, 300–331; 623/17.11–17.16
See application file for complete search history.

(56) References Cited

U.S. PATENT DOCUMENTS 2,472,103 A 6/1949 Giesen
2,484,655 A 10/1949 Shreve
(Continued)

FOREIGN PATENT DOCUMENTS

FR 2 876 897 A1 4/2006
FR 2 916 956 A1 12/2008
(Continued)

OTHER PUBLICATIONS

International Patent Application No. PCT/US2011/032627: International Search Report dated Mar. 30, 2012, 6 pages.
(Continued)

*Primary Examiner* — Christopher Beccia
(74) *Attorney, Agent, or Firm* — Raymond N. Scott, Jr.

(57) ABSTRACT

A fixation assembly having a driver, a holding sleeve, and an alignment mechanism is disclosed. The driver may include a driver body and a coupling extending from a distal end of the driver body. The holding sleeve may have a holding sleeve body, a channel extending through the holding sleeve body, and a fixation element coupler disposed at a distal portion of the holding sleeve body. The channel may be configured to receive the driver, and the fixation element coupler may be configured to temporarily hold a fixation element. The alignment mechanism may extend from the holding sleeve, and may have at least one alignment member configured to engage an underlying structure to which the fixation element is to be affixed so as to align the fixation element and driver assembly with respect to the underlying structure.

20 Claims, 17 Drawing Sheets

(51) Int. Cl.
*A61F 2/44* (2006.01)
*A61F 2/30* (2006.01)
*A61B 17/70* (2006.01)
*A61B 17/68* (2006.01)

(52) U.S. Cl.
CPC ............... *A61F2002/30331* (2013.01); *A61F 2002/30387* (2013.01); *A61F 2002/30494* (2013.01); *A61F 2002/30509* (2013.01); *A61F 2002/30514* (2013.01); *A61F 2002/30517* (2013.01); *A61F 2002/30578* (2013.01); *A61F 2002/30604* (2013.01); *A61F 2002/30616* (2013.01); *A61F 2002/30772* (2013.01); *A61F 2002/30777* (2013.01); *A61F 2002/30787* (2013.01); *A61F 2002/30836* (2013.01); *A61F 2002/30841* (2013.01); *A61F 2002/30843* (2013.01); *A61F 2002/30845* (2013.01); *A61F 2002/30879* (2013.01); *A61F 2002/30904* (2013.01); *A61F 2002/4475* (2013.01); *A61F 2002/4627* (2013.01); *A61F 2002/4628* (2013.01); *A61F 2310/00017* (2013.01); *A61F 2310/00023* (2013.01); *A61F 2310/00359* (2013.01)

(56) References Cited

U.S. PATENT DOCUMENTS

| | | | |
|---|---|---|---|
| 4,704,929 A | 11/1987 | Osada | |
| 5,536,127 A | 7/1996 | Pennig | |
| 5,672,176 A | 9/1997 | Biedermann et al. | |
| 6,048,344 A | 4/2000 | Schenk | |
| 6,306,140 B1 * | 10/2001 | Siddiqui | 606/315 |
| 6,440,132 B1 | 8/2002 | Jackson | |
| 6,730,127 B2 * | 5/2004 | Michelson | 623/17.16 |
| 7,137,322 B2 | 11/2006 | Mark et al. | |
| 7,846,207 B2 * | 12/2010 | Lechmann et al. | 623/17.11 |
| 2002/0004683 A1 | 1/2002 | Michelson | |
| 2005/0261695 A1 | 11/2005 | Cragg et al. | |
| 2006/0149264 A1 | 7/2006 | Castaneda et al. | |
| 2006/0293748 A1 | 12/2006 | Alexander et al. | |
| 2007/0162010 A1 | 7/2007 | Chao et al. | |
| 2007/0276386 A1 | 11/2007 | Gerlach et al. | |
| 2009/0105832 A1 | 4/2009 | Allain et al. | |
| 2010/0228297 A1 | 9/2010 | Bray et al. | |
| 2011/0112587 A1 * | 5/2011 | Patel et al. | 606/86 A |

FOREIGN PATENT DOCUMENTS

| | | |
|---|---|---|
| WO | WO 02/04683 A1 | 1/2002 |
| WO | WO 2006/047640 | 5/2006 |
| WO | WO 2010/054181 A1 | 5/2010 |
| WO | WO 2010/071707 | 6/2010 |
| WO | WO 2010/092893 | 8/2010 |
| WO | WO 2010/121028 | 10/2010 |

OTHER PUBLICATIONS

International Patent Application No. PCT/US2011/032627: International Preliminary Report on Patentability & Written Opinion dated Oct. 15, 2013, 8 pages.

* cited by examiner

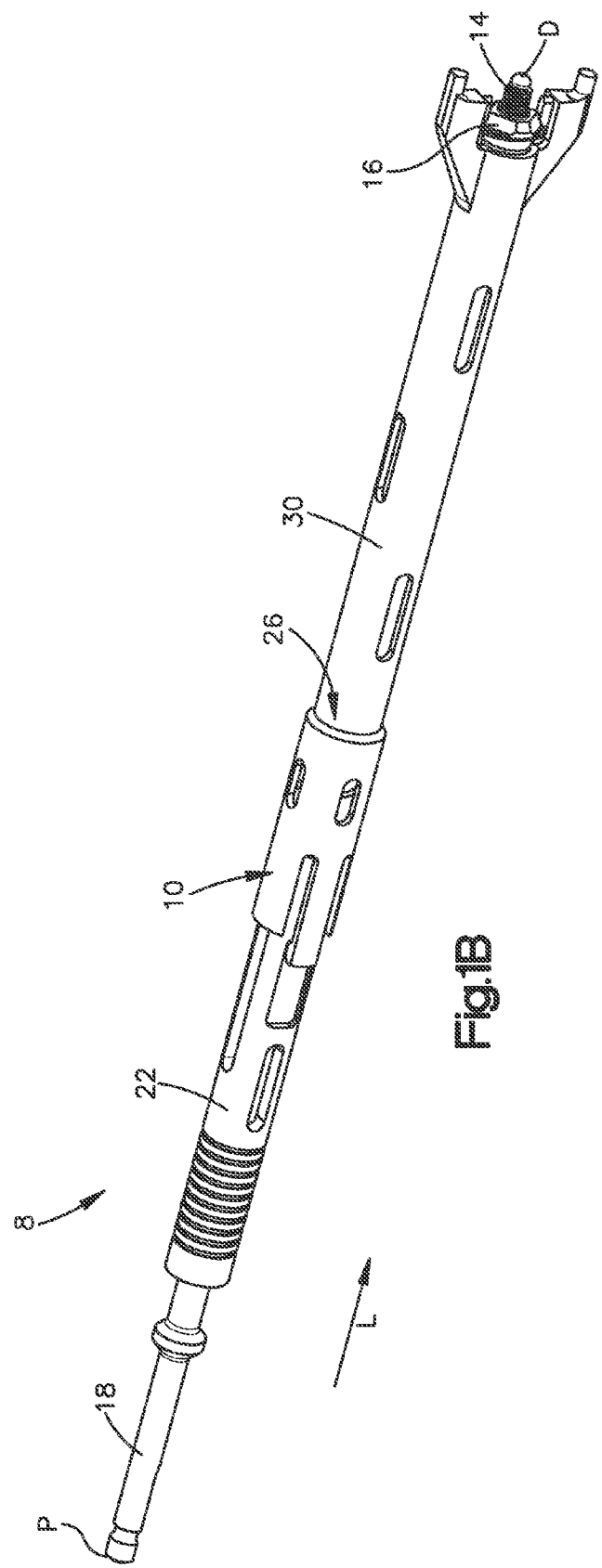

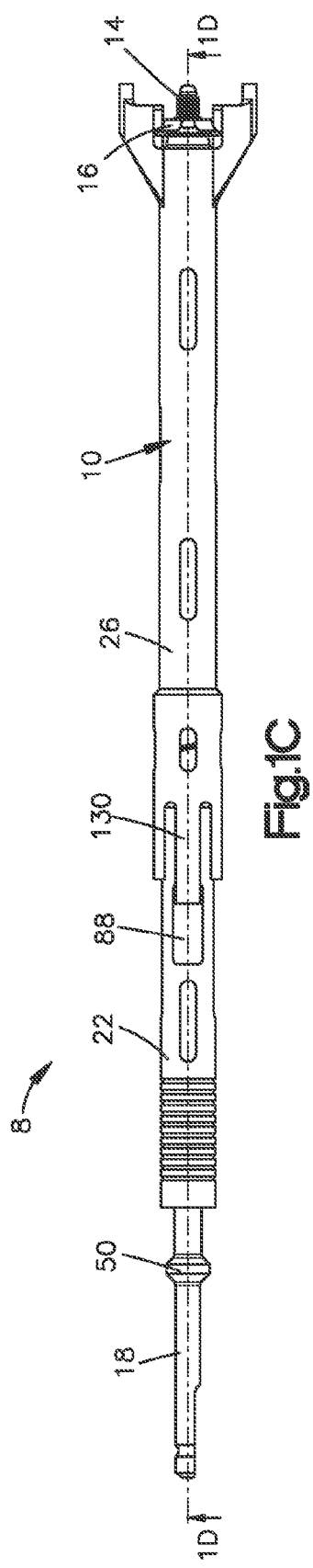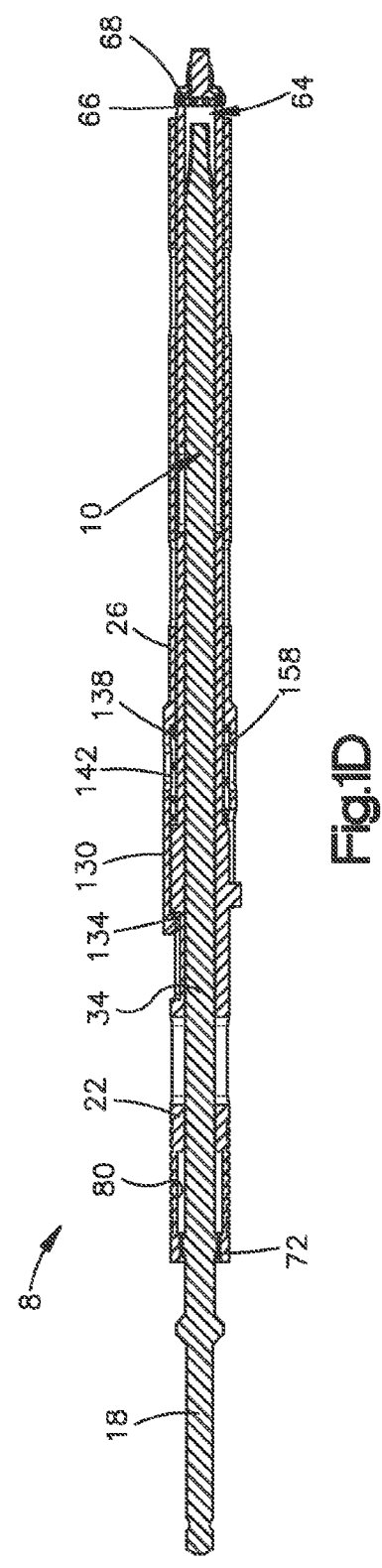

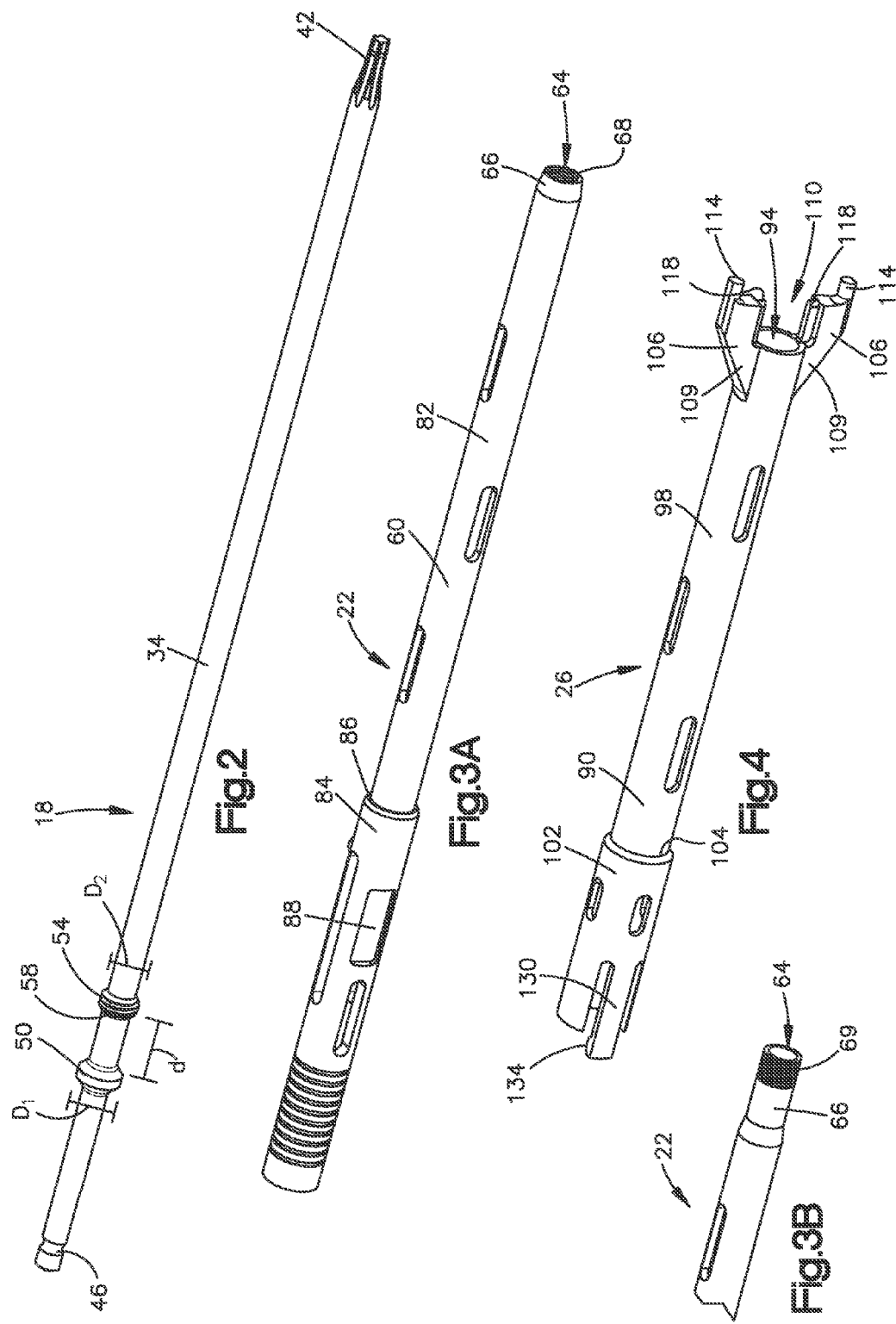

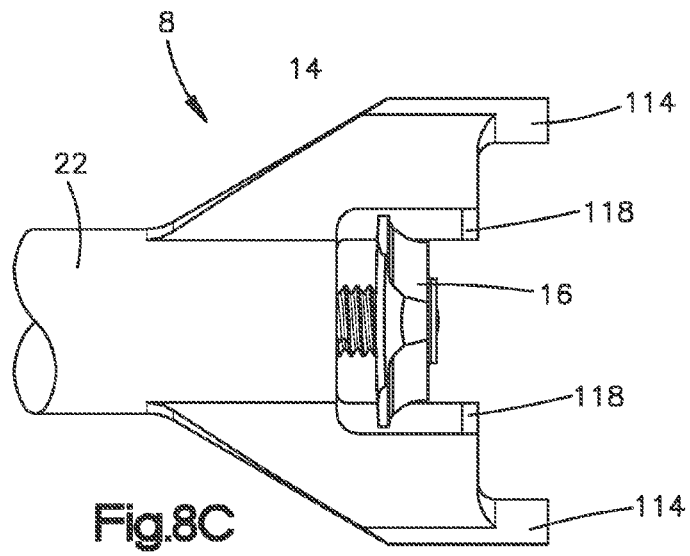
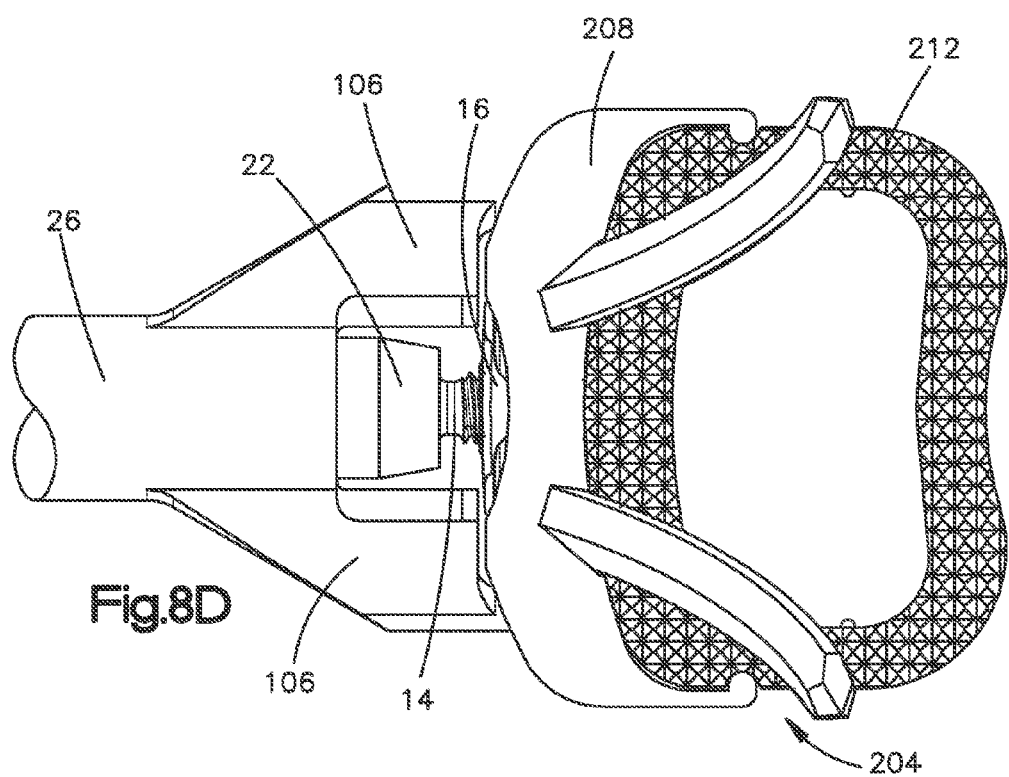

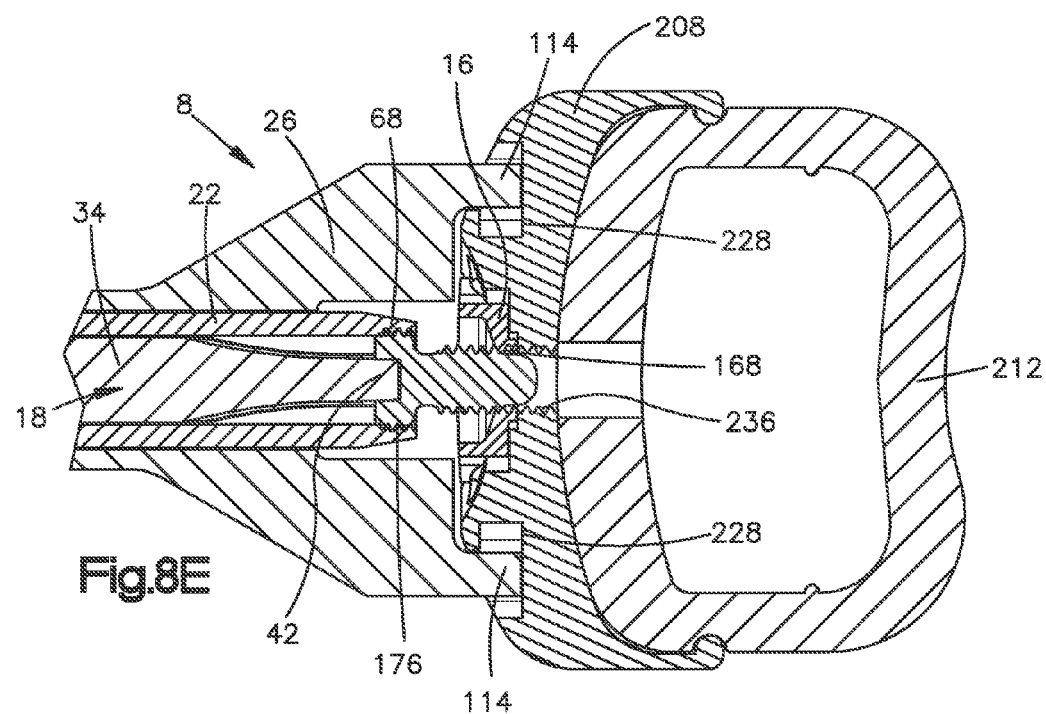
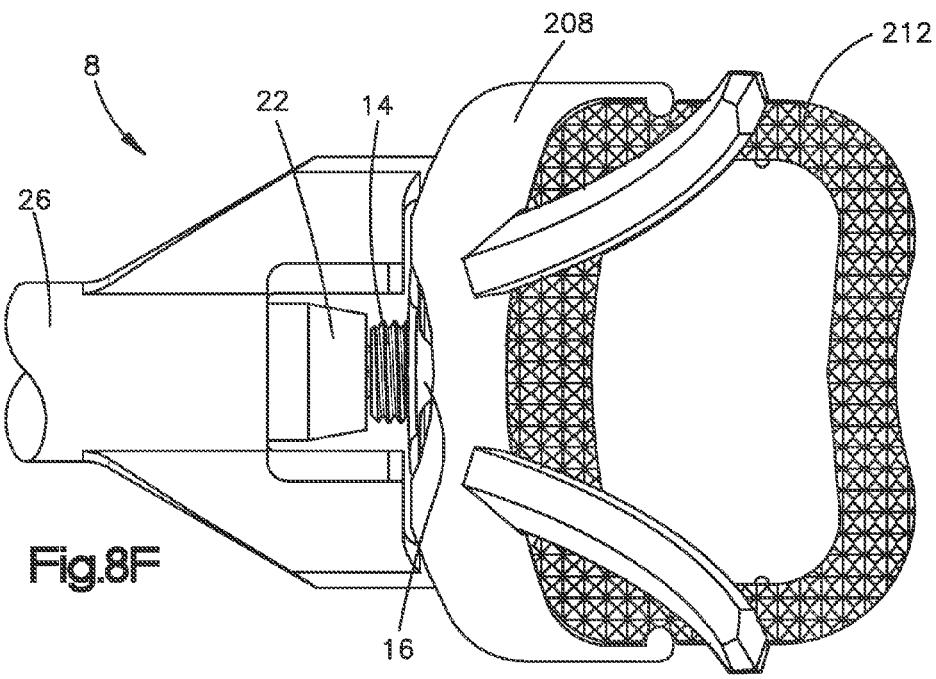

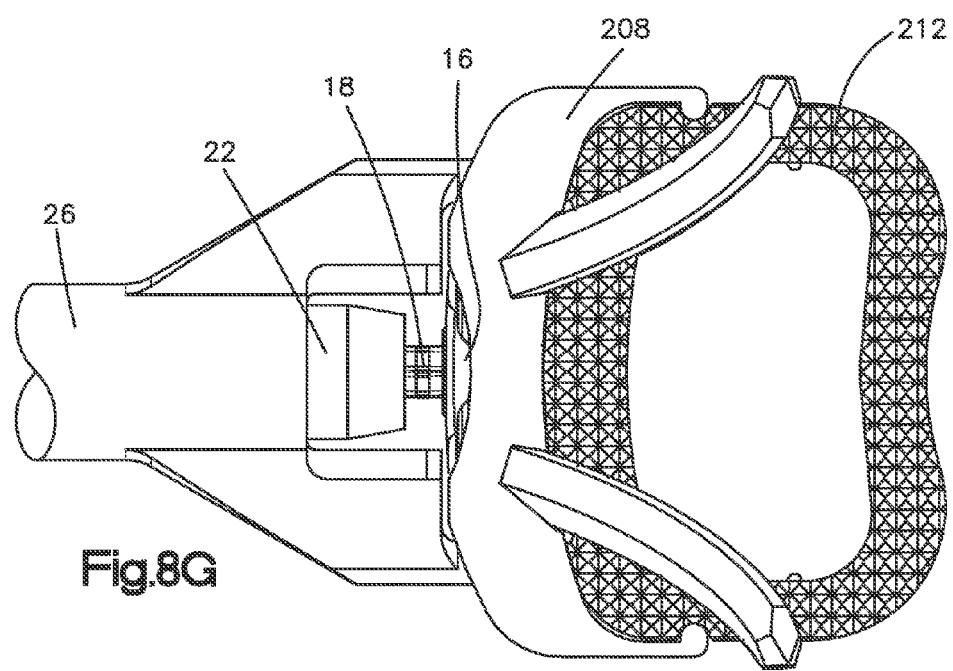

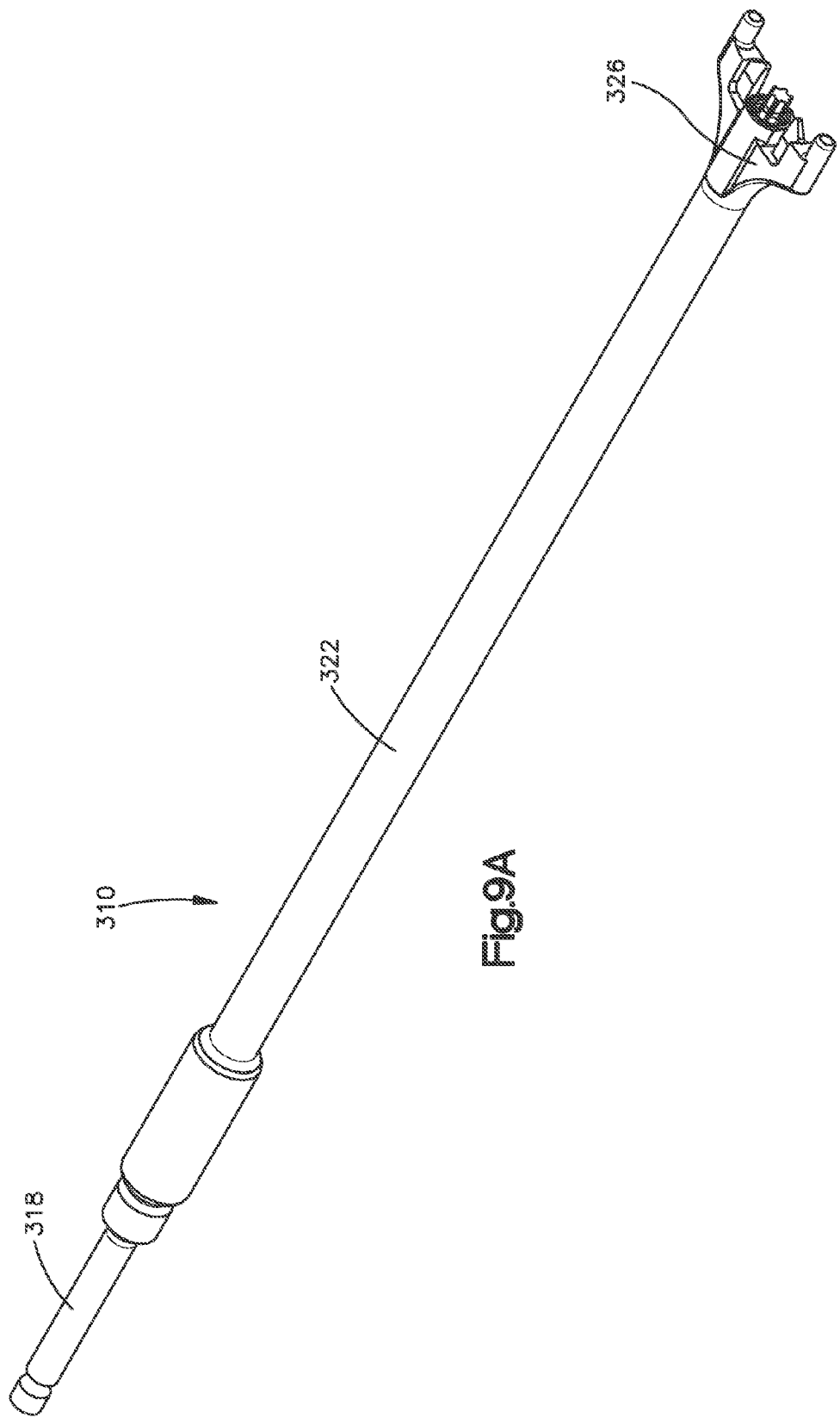

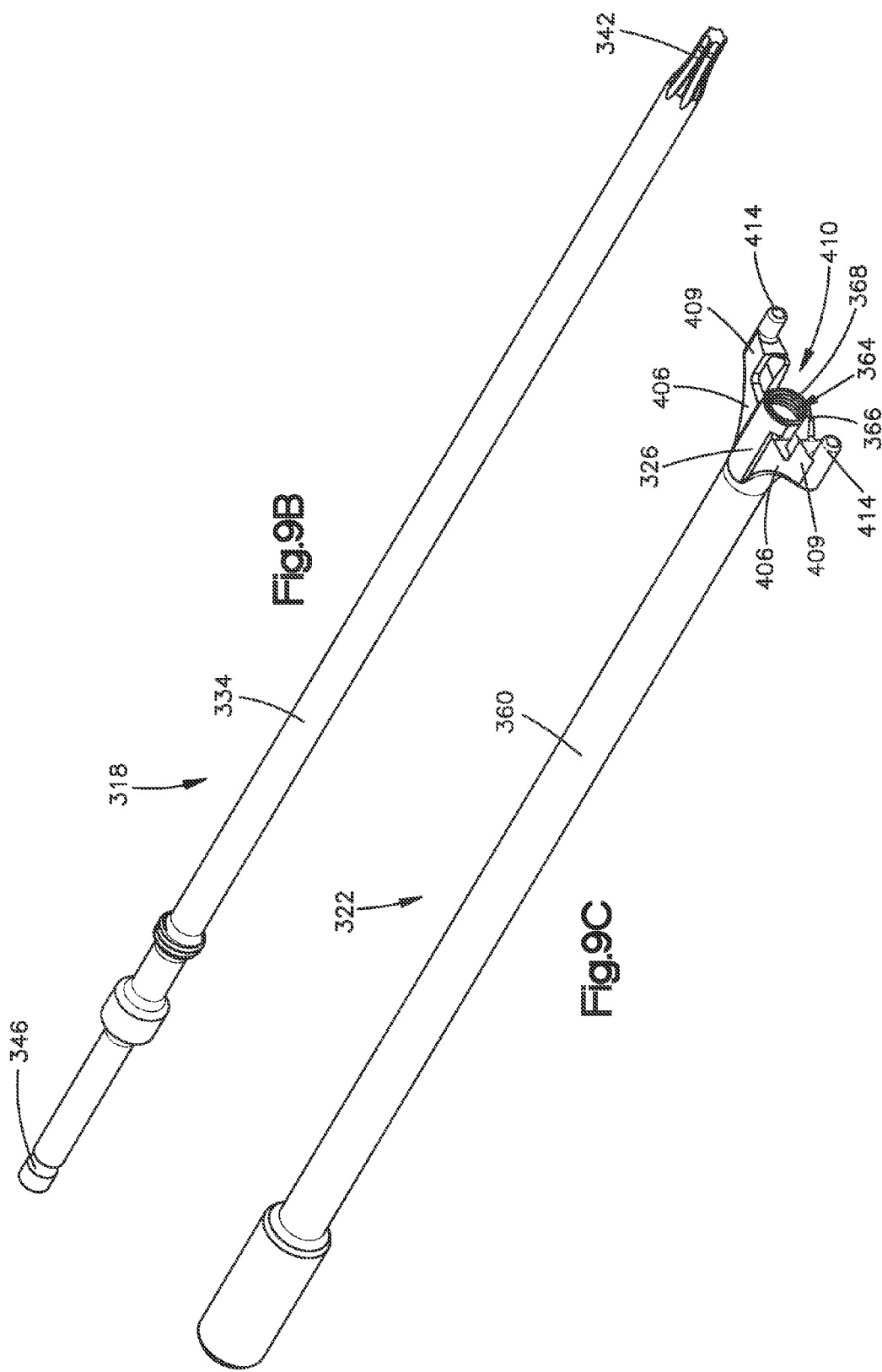

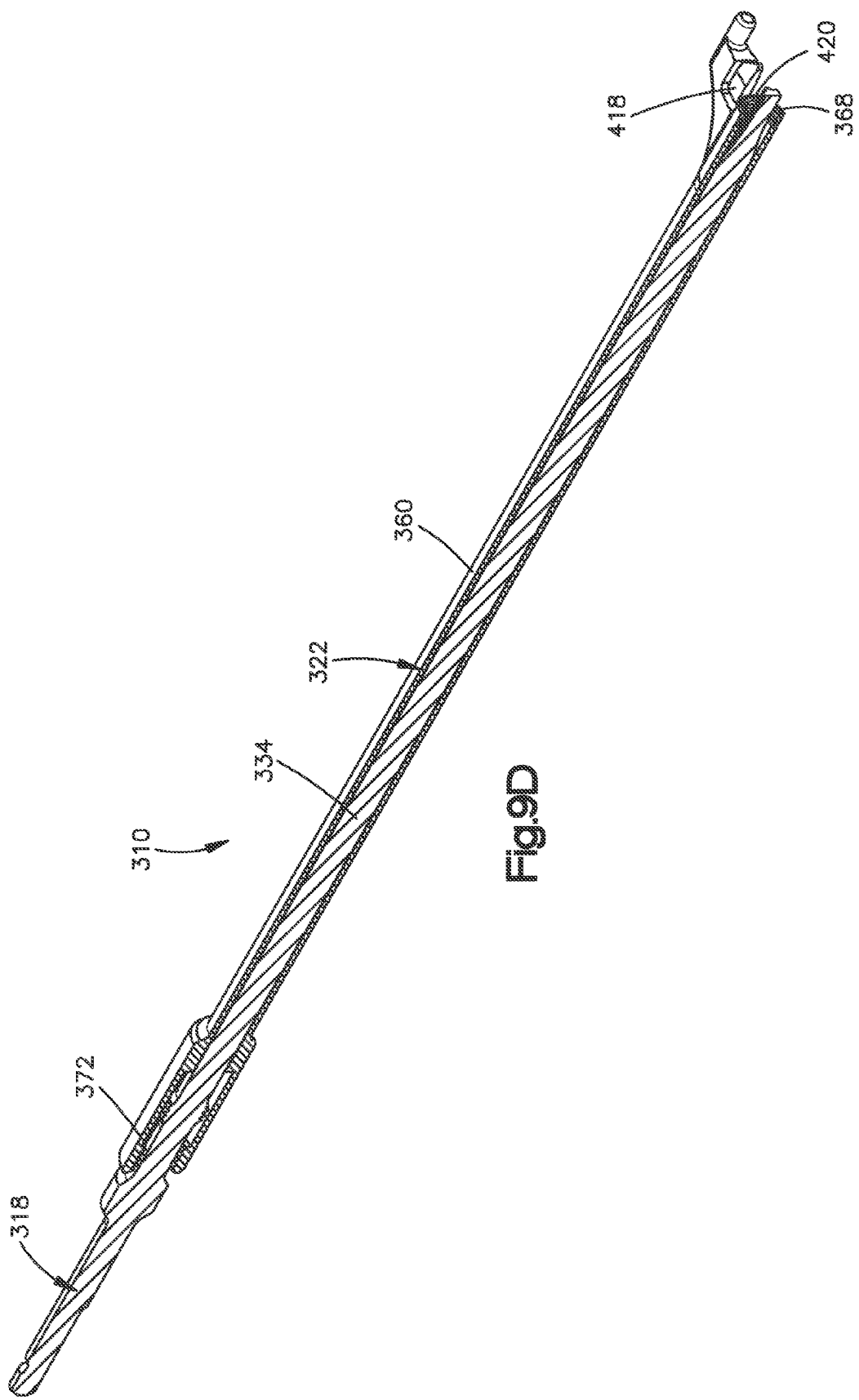

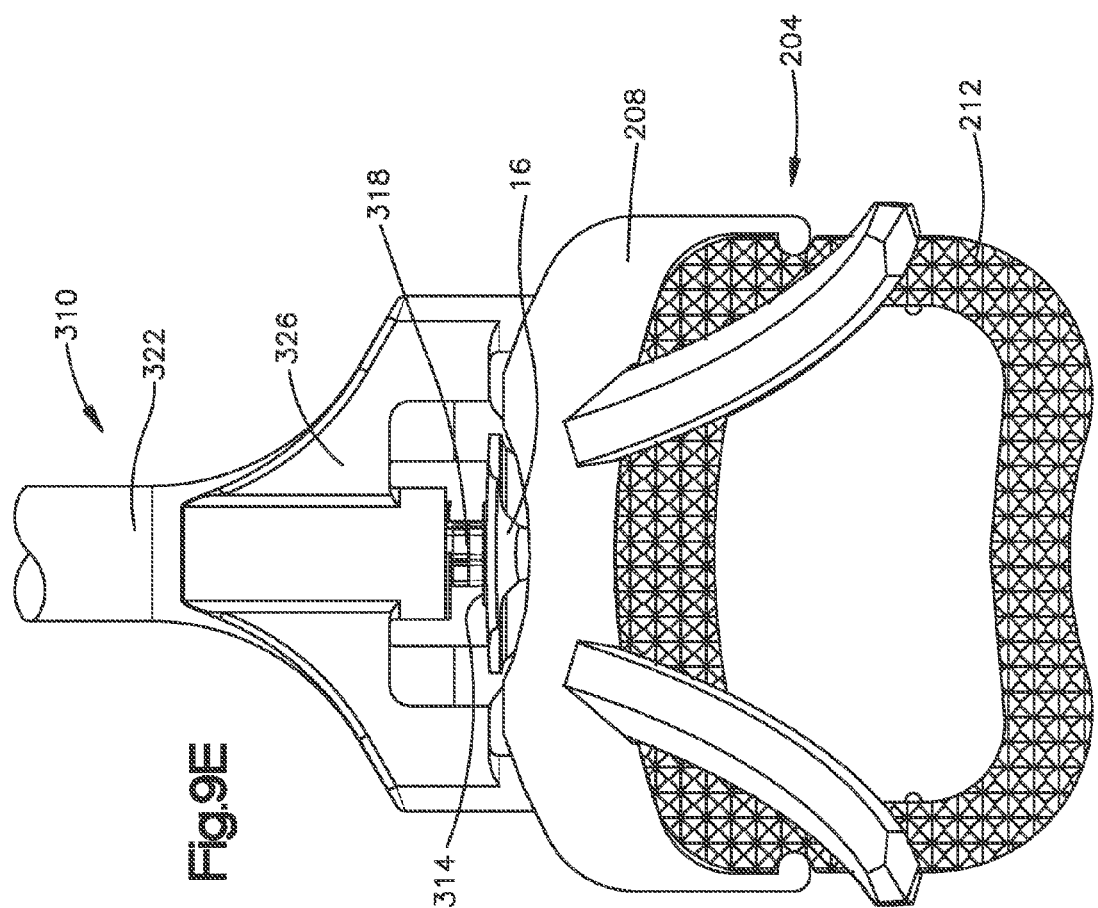

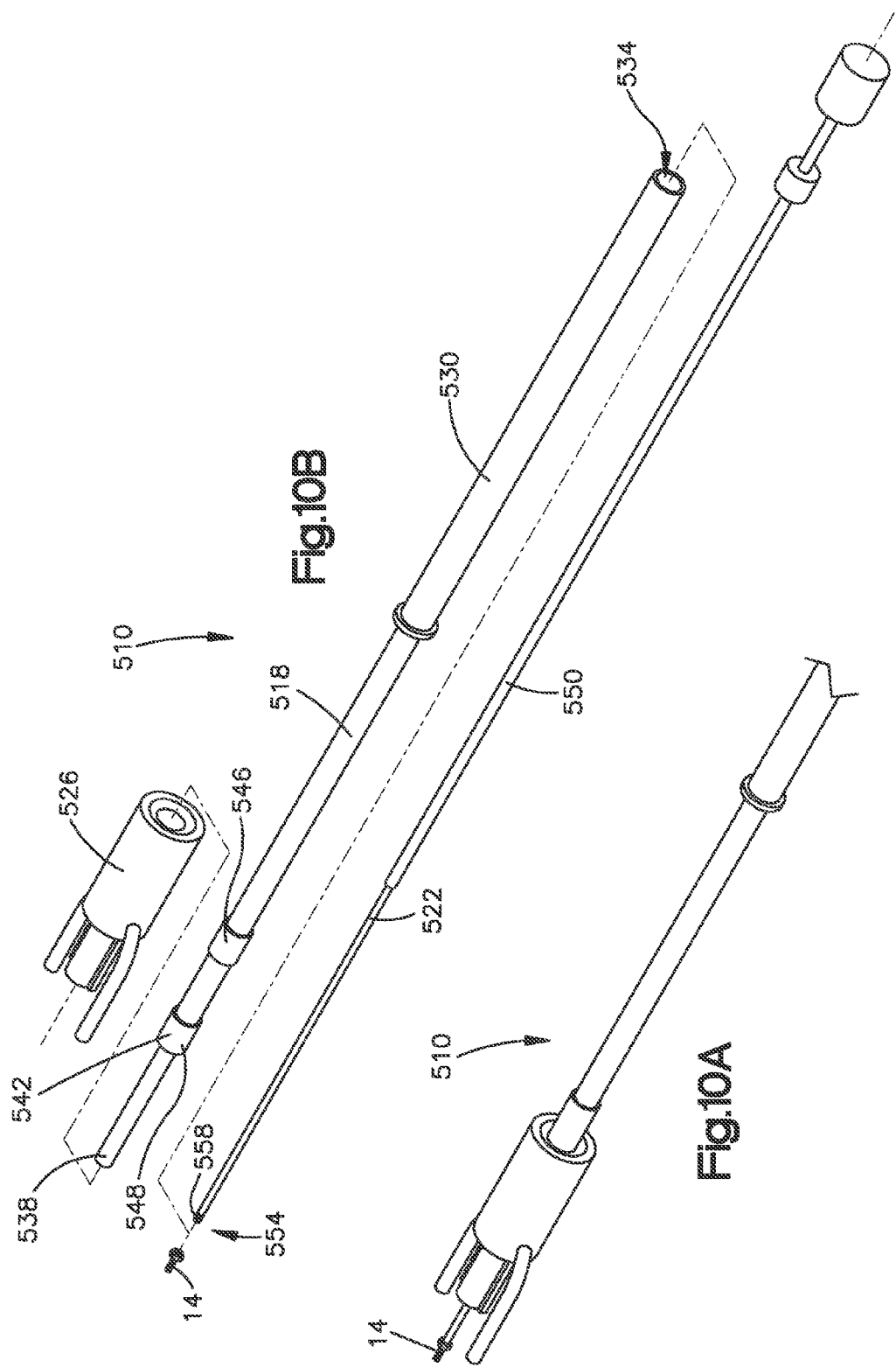

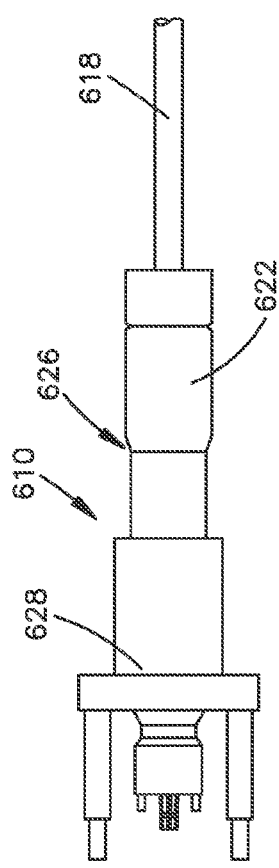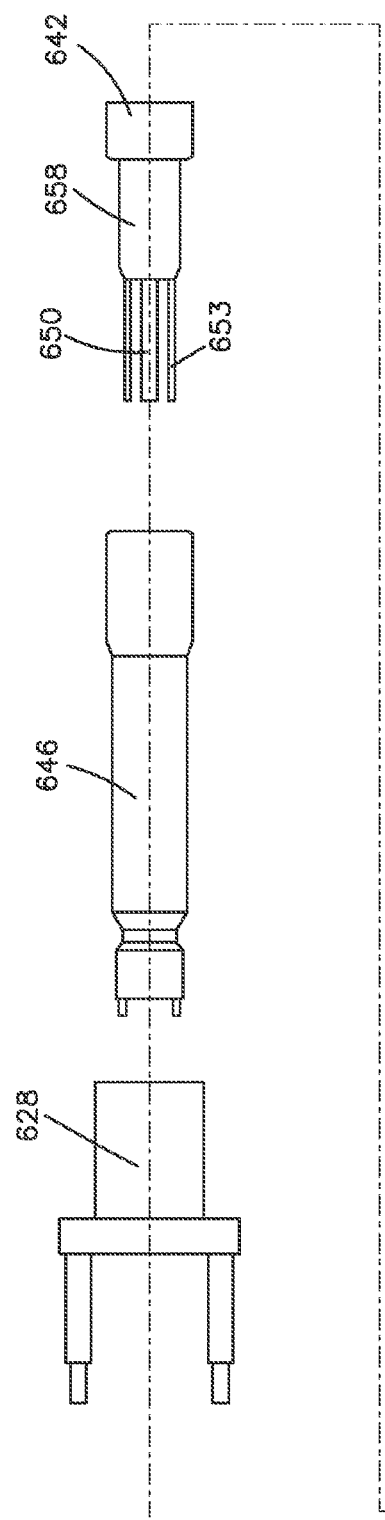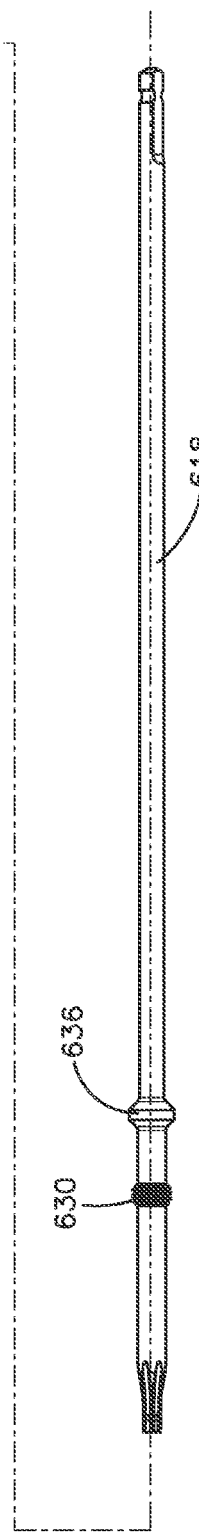

FIXATION ASSEMBLY

CROSS REFERENCE TO RELATED APPLICATIONS

This application is a continuation of U.S. patent application Ser. No. 13/087,659, filed Apr. 15, 2011, pending. The aforementioned patent application is incorporated herein by reference.

BACKGROUND OF THE INVENTION

During many medical procedures, fixation elements such as screws may be used to affix certain devices, such as implants, to an underlying structure such as bone or even another implant. In certain vertebral fixation procedures, once fixation members have securely attached an implant to the underlying structure, a blocking plate is affixed to the implant using a screw to thereby prevent the fixation members from backing out of the implant. For example, the blocking plate can be attached to an intervertebral implant after the implant has been affixed to a superior vertebral body and an inferior vertebral body using one or more fixation members. Such screws are typically affixed using drivers that securely hold the screw so as to prevent the screw from inadvertently falling into the patient prior to the placement of the screw.

Devices for retaining screws on a screw driver are known, but many of the prior devices depend on a linear side-bearing force from a clamp or other mechanism to hold the screw in place. Other methods of temporarily retaining a screw to a driver include using a central threaded rod down the center of the driver or a driver with a spring-wire off axis of the driver that may protrude laterally into the screw.

SUMMARY OF THE INVENTION

A fixation assembly configured to temporarily hold, align and affix a fixation element to an underlying structure such as an implant is disclosed. The fixation assembly may include a driver, a holding sleeve, and an alignment mechanism. The driver may include a longitudinally elongate driver body, and a coupling that extends distally from a distal end of the driver body. The coupling may be configured to engage a coupling defined by a head of the fixation element.

The holding sleeve may include a holding sleeve body and a channel that extends longitudinally through the holding sleeve body. A distal end of the holding sleeve body defines a fixation element coupler that is configured to temporarily attach the fixation element to the holding sleeve. In one embodiment, the fixation element coupler includes internal threads defined by the channel of the holding sleeve. The threads of the holding sleeve may be configured to engage external threads defined by the head of the fixation element. The driver is configured to extend through the channel of the holding sleeve and couple to the holding sleeve to thereby define a driver and holding sleeve assembly. The driver may be coupled to the holding sleeve such that the driver may translate a predetermined distance with respect to the holding sleeve.

The alignment mechanism may include an alignment mechanism body and a channel that extends through the alignment mechanism body. The channel is configured to receive the driver and holding sleeve assembly. The alignment mechanism further includes a pair of alignment members that extend distally past a distal end of the holding sleeve. The alignment members may be configured to engage apertures defined by a fixation plate of an intervertebral implant.

The fixation assembly may be configured to affix a fixation element having a shaft and a head disposed at a proximal end of the shaft. The shaft may include threads that are configured to engage threads defined by the fixation plate of the intervertebral implant. Similarly, the head may include threads that are configured to engage threads defined by the fixation element coupler of the holding sleeve. The pitch of the threads on the head and on the shaft may be similar such that the rate at which the fixation element is advanced into the fixation plate, is similar to the rate that the fixation element disengages from the holding sleeve.

In another embodiment, the fixation assembly may include a driver, a fixation element coupler, and an alignment mechanism. The driver may have a driver body and a coupling extending from a distal end of the driver body. The coupling may be configured to engage a coupling defined by a fixation element. The fixation element coupler may be configured to temporarily hold the fixation element. At least one of the driver and the fixation element coupler may be translatable relative to the other. The alignment mechanism may have at least one alignment member configured to engage an underlying structure to which the fixation element is to be affixed so as to align the fixation element, the driver, and the fixation element coupler with respect to the underlying structure.

BRIEF DESCRIPTION OF THE DRAWINGS

The foregoing summary, as well as the following detailed description of a preferred embodiment of the application, will be better understood when read in conjunction with the appended drawings. For the purposes of illustrating the fixation assemblies of the present application, there is shown in the drawings preferred embodiments. It should be understood, however, that the application is not limited to the precise arrangements and instrumentalities shown. In the drawings:

FIG. 1B is a perspective view of the fixation assembly shown in FIG. 1A, the fixation assembly including at least one fixation element, a blocking plate, and a driver assembly that is configured to securely hold, align, and drive the fixation element, the driver assembly including a driver, a holding sleeve disposed about the driver, and an alignment mechanism that is configured to engage a structure, such as the intervertebral implant shown in FIG. 1A, to which the fixation element is to be affixed;

FIG. 1C is a top plan view of the driver assembly shown in FIG. 1B;

FIG. 1D is a sectional side elevation view of the driver assembly shown in FIG. 1C taken through the line 1D-1D;

FIG. 2 is a perspective view of the driver shown in FIG. 1A;

FIG. 3A is a perspective view of the holding sleeve shown in FIG. 1A;

FIG. 3B is a perspective view of the holding sleeve in accordance with another embodiment;

FIG. 4 is a perspective view of the alignment mechanism shown in FIG. 1A;

FIG. 8C is a top plan view of a portion of the fixation assembly illustrated in FIG. 8B, showing the alignment mechanism translated distally;

FIG. 8D is a top plan view of a portion of the fixation assembly illustrated in FIG. 8C, showing the alignment mechanism engaging the fixation plate of the intervertebral implant of FIG. 7;

FIG. 8E is a sectional top plan view of the portion of the fixation assembly illustrated in FIG. 8D, showing the alignment mechanism engaging the fixation plate of the intervertebral implant;

FIG. 8F is a top plan view of a portion of the fixation assembly illustrated in FIG. 8D, showing the driver affixing the fixation element and the blocking plate to the fixation plate of the intervertebral implant;

FIG. 8G is a top plan view of a portion of the fixation assembly illustrated in FIG. 8F, showing the fixation element and the blocking plate fully affixed to the intervertebral implant;

FIG. 9A is a perspective view of a fixation assembly constructed in accordance with another embodiment, the fixation assembly including a driver assembly that is configured to securely hold, align, and drive a fixation element, the driver assembly including a driver, and a holding sleeve disposed about the driver, the holding sleeve including an integrated alignment mechanism that is configured to engage a structure to which the fixation element is to be affixed;

FIG. 9B is a perspective view of the driver shown in FIG. 9A;

FIG. 9C is a perspective view of the holding sleeve shown in FIG. 9A;

FIG. 9D is a sectional perspective view of the driver assembly shown in FIG. 9A taken through the line 9D-9D;

FIG. 9E is a top plan view of the fixation assembly shown in FIG. 9A affixing a fixation element to an intervertebral implant;

FIG. 10A is a perspective view of a driver assembly constructed in accordance with another embodiment, the driver assembly including a driver, a holding rod extending through a channel of the driver, and an alignment mechanism disposed about the driver;

FIG. 10B is an exploded assembly view of the driver assembly shown in FIG. 10A;

FIG. 11A is a perspective view of a driver assembly in accordance with another embodiment, the driver assembly including a driver, a two part tube capable of rotating about the driver, and an alignment mechanism; and FIG. 11B is an exploded assembly view of the driver assembly shown in FIG. 11A.

DETAILED DESCRIPTION OF THE INVENTION

Figure 1A:
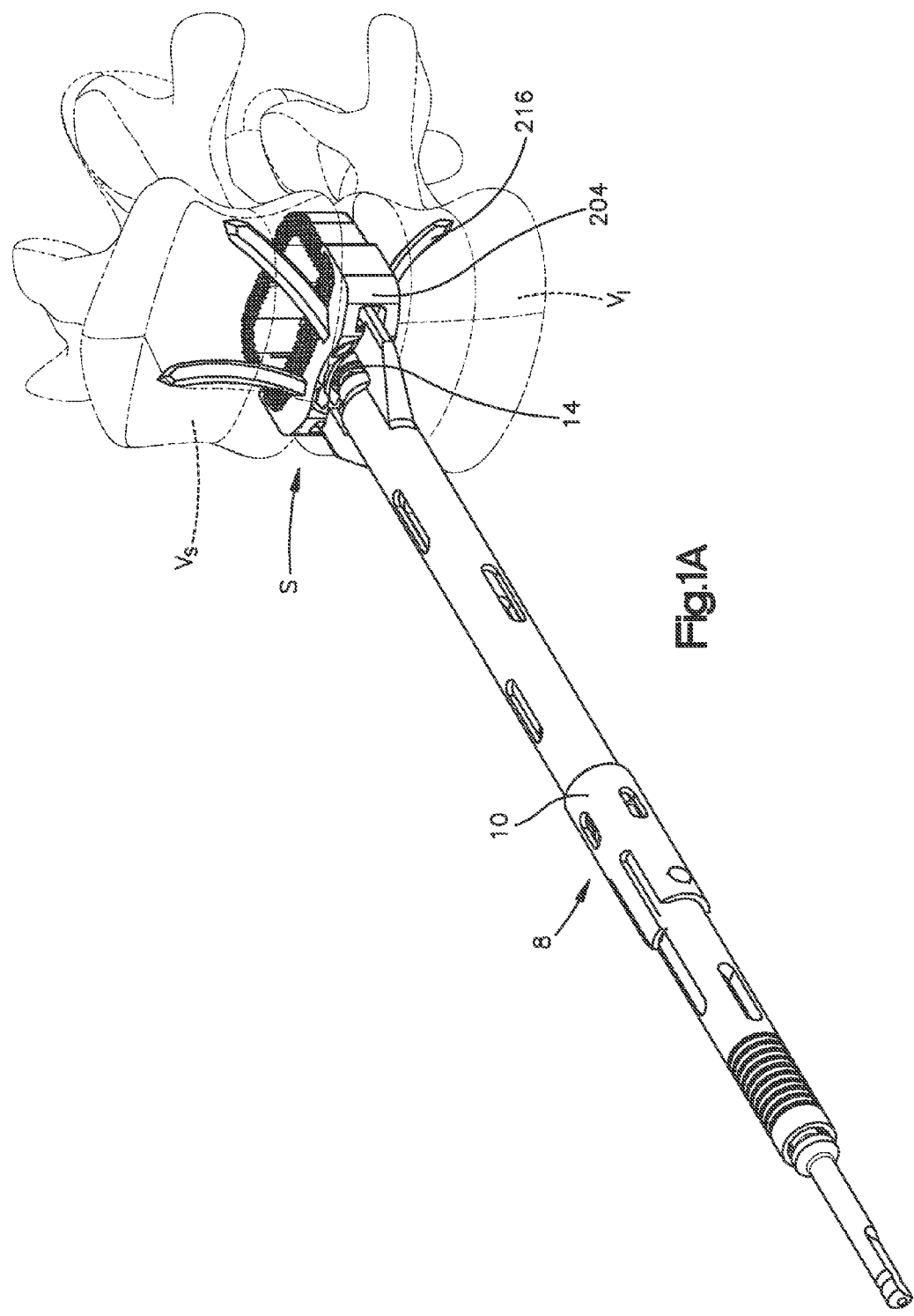
FIG. 1A is a perspective view of a fixation assembly constructed in accordance with one embodiment, the fixation assembly engaging an intervertebral implant that is disposed in an intervertebral space.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the bone anchor and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

As shown in FIGS. 1A-1D, a fixation assembly 8 includes a fixation element 14 and a driver assembly 10 that is configured to securely hold, align, and drive the fixation element 14 into an underlying structure, which can be any desired bone such as a vertebral body, an implant, soft tissue, or any alternative underlying structure configured to receive the fixation element 14. As shown in FIG. 1A, the driver assembly 10 may be configured affix the fixation element 14 to an intervertebral implant 204 that is anchored within an intervertebral space "S" that is defined between adjacent vertebral bodies $V_S$ and $V_I$.

The driver assembly 10 is elongate in a longitudinal direction L and defines a proximal end P and a distal end D that is opposite the proximal end P along the longitudinal direction L and is configured to retain the fixation element 14 so as to define a driving end of the driver assembly 10. The driver assembly 10 is configured to securely hold the fixation element 14 and then subsequently align and seat the fixation element 14 in the underlying structure. It should be appreciated that the fixation element 14 can be permanently driven into the underlying structure, such that the fixation element 14 remains implanted after the surgical procedure has been completed. For instance, the fixation element 14 can be temporarily coupled to the driver assembly 10 prior to seating the fixation element 14 into its permanent placement. By temporarily coupling the fixation element 14 to the driver assembly 10 during placement, the fixation element 14 will not inadvertently disengage from the driver assembly 10 and fall into a patient.

The driver assembly 10 may be operable to align and seat a variety of fixation elements 14 that are utilized in a variety of applications. For instance, the fixation assembly 8 can further include a blocking plate 16, and the driver assembly 10 may be configured to seat or otherwise drive a screw into a fixation plate of the intervertebral implant 204 shown in FIG. 1A to thereby affix the blocking plate 16 to the fixation plate. The blocking plate 16 can prevent fixation members, such as fixation members 216 that attach the implant 204 to the vertebra $V_S$ and $V_1$ from backing out after being implanted in the underlying structure.

As shown in FIGS. 1B-1D, the driver assembly 10 includes a driver 18 and a holding sleeve 22 that is disposed about the driver 18. The holding sleeve 22 is configured to hold or otherwise support the fixation element 14 while the driver 18 is configured to drive the fixation element 14. For instance, the driver 18 is configured to drive the fixation element 14 so as to cause the fixation element 14 to disengage from the holding sleeve 22 while simultaneously engaging the underlying structure to which it is to be affixed. As shown in FIG. 1B, the driver assembly 10 can further include an alignment mechanism 26 that is configured to engage the underlying structure to which the fixation element 14 is to be affixed, so as to align the fixation element 14 as it is being driven by the driver 18. In the illustrated embodiment, the alignment mechanism 26 defines an alignment sleeve 30 that at least partially surrounds or encircles a distal portion of the holding sleeve 22. Though it should be understood that the alignment mechanism 26 and the holding sleeve 22 may be one solid piece (e.g. as shown in FIG. 9D). The driver 18, the holding sleeve 22, and the alignment mechanism 26 may be made from any biocompatible material, such as titanium, steel, or aluminum.

As shown in FIG. 2, the driver 18 includes a driver body 34 that is elongate in the longitudinal direction L, and defines respective proximal and distal ends separated from each other along the longitudinal direction L. The driver 18 further includes a coupling 42 that extends distally from the distal end of the driver body 34 and an engagement member 46 that extends proximally from the proximal end of the driver body 34. The driver 18 may be made from any biocompatible material, such as titanium, steel, or aluminum.

The coupling 42 of the driver 18 is configured to mate with a complimentary coupling of the fixation element 14. Once the coupling 42 of the driver 18 has mated with the fixation element 14, the driver 18 is configured to receive a torsional force or torque, and impart the torsional force or torque to the fixation element 14. In the illustrated embodiment, the coupling 42 is substantially star-shaped, though it should be understood that the coupling 42 may define any suitable alternative shape as desired, such as a cruciform, a hex, or the like.

The engagement member 46 is configured to be received by or otherwise attach to a complementary engagement member of a handle. Therefore, when the driver assembly 10 is to be used, an individual may attach the handle to the driver 18 by attaching the engagement member of the handle to the engagement member 46 of the driver 18. As shown, the engagement member 46 may define a hexagon, though it should be understood that the engagement member 46 may define other shapes that allow the driver 18 to be coupled to a handle.

As shown in FIG. 2, the driver 18 further includes a first protrusion 50 that extends radially outward from the driver body 34 proximate to the proximal end of the driver body 34, and a second protrusion 54 that extends radially outward from the driver body 34 at a location that is distal to the first protrusion 50. As shown, the first protrusion 50 and the second protrusion 54 are spaced apart along the driver body 34 by a distance d. The first and second protrusions 50 and 54 can be annular or alternatively shaped, such that the first protrusion 50 is generally smooth and defines a first diameter or alternative cross-sectional dimension $D_1$, and the second protrusion 54 includes threads 58 and defines a second diameter or alternative cross-sectional dimension $D_2$ that is less than the first cross-section dimension $D_1$. The first and second protrusions 50 and 54 are configured to limit the translation of the driver 18 within the holding sleeve 22 in the longitudinal direction L.

As shown in FIGS. 1B-1D, and 3A, the holding sleeve 22 is elongate in the longitudinal direction L and is configured to receive the driver 18 such that either or both of the driver 18 or the holding sleeve 22 can translate in the longitudinal L direction relative to the other. As shown in FIG. 1D, the holding sleeve 22 includes a holding sleeve body 60 and a channel 64 that extends through the holding sleeve body 60 in the longitudinal direction L. The distal end of the holding sleeve body 60 defines a fixation element coupler 66 that is configured to temporarily hold a fixation element. In the illustrated embodiment, the fixation element coupler 66 includes internal threads 68 defined within the distal end of the channel 64. The internal threads 68 are configured to engage external threads of the fixation element 14 to thereby securely hold the fixation element 14 to the holding sleeve 22. Though it should be understood that the fixation element coupler 66 may include external threads 69 that are configured to engage internal threads of the fixation element 14, as shown in FIG. 3B. Similarly, the proximal end of the channel 64 defines a coupling feature such as internal threads 72 that are configured to be engaged by the threads 58 of the second protrusion 54 of the driver 18 so as to couple the holding sleeve 22 to the driver 18. The channel 64 defines a recessed portion 80 distal to the threads 72, that has a diameter capable of allowing the driver 18, and more particularly the second protrusion 54 of the driver 18 to translate and rotate freely within the holding sleeve 22 for a predetermined distance.

To couple the driver 18 to the holding sleeve 22 to thereby form a driver-holding sleeve assembly, the driver 18 is inserted into the channel 64 of the holding sleeve 22 through a proximal opening of the channel 64. The driver 18 is advanced through the channel 64 by simple translation of the driver 18 until the internal threads 72 of the channel 64 abut the threads 58 of the driver 18. The driver 18 may then be rotated until the second protrusion 54 of the driver 18 is threaded past the threads 72 of the channel 64 and the second protrusion 54 is disposed within the recessed portion 80 of the channel 64. As shown in FIG. 1D, while the second protrusion 54 of the driver 18 is disposed within the recessed portion 80, the driver 18 may be translated distally until the first protrusion 50 abuts a proximal end of the holding sleeve 22. Thus, the first protrusion 50 defines a stop configured to abut the proximal end of the holding sleeve 22 when the driver is fully inserted into the holding sleeve 22.

Referring now to FIGS. 1C, 1D and 3A, the holding sleeve body 60 defines a distal portion 82 and a proximal portion 84. The distal portion 82 has a diameter or cross-sectional dimension that is less than the diameter or cross-sectional dimension of the proximal portion 84 such that a shoulder 86 is defined at the juncture of the distal and proximal portions 82, 84. The holding sleeve body 60 defines a groove or slot 88 extending through the proximal portion 84 that is configured to be engaged by a spring finger defined by the alignment mechanism 26. The interaction between the spring finger of the alignment mechanism 26 and the groove 88 limits the longitudinal translation of the alignment mechanism 26 as will be described.

As shown in FIGS. 1B-1D, and 4, the alignment mechanism 26 includes an alignment body 90, and defines a channel 94 that extends through the alignment body 90 in the longitudinal direction L. The alignment body 90 includes a first section 98 and a second section 102 that is disposed proximal with respect to the first section 98, such that the first and second sections 98 and 102 join at a juncture 104. The second section 102, has a diameter or other cross-sectional dimension that is greater than the diameter or other cross-sectional dimension of the first section 98. In particular, the channel 94 of the second section 102, has a diameter or other cross-sectional dimension that is greater than the channel 94 of the first section 98. The channel 94 of the alignment mechanism 26 is configured to receive the holding sleeve 22 such that the alignment mechanism 26 may translate distally or proximally a predetermined distance.

As shown in FIG. 4, the alignment mechanism 26 further includes a pair of struts 106 that each have a strut body 109 that extends laterally out from the holding sleeve 22. In particular, each strut body 109 extends laterally out from the distal portion 98 of the alignment mechanism body 90. As shown, the struts 106, also extend distally past the distal end of the alignment body 90. The struts 106 are separated along a lateral direction that is substantially perpendicular with respect to the longitudinal direction, such that a gap 110 is defined between the two struts 106 adjacent a distal opening of the channel 94. As shown, each strut 106 includes an alignment member 114 that extends distally from the strut body 109. In the illustrated embodiment, the alignment members 114 are pegs or cylindrical rods, however, it should be understood that the alignment members 114 may define any shape as desired. The alignment members 114 are configured to engage the underlying structure to which the fixation element 14 is to be affixed so as to align the driver assembly 10 as well as the fixation element 14 to the underlying structure when the fixation element 14 is to be affixed to the underlying structure.

As shown in FIG. 4, the alignment mechanism 26 can further include a rail 118 that extends out from at least one of the strut bodies 109 and into the gap 110. As shown, the two rails 118 extend parallel to each other in the longitudinal direction L, and are disposed opposite to each other within the gap 110. The rails 118, and thus the alignment mechanism 26, are configured to engage the blocking plate 16 as the fixation element 14 is temporarily coupled to the holding sleeve 22. As the fixation element 14 is advanced into an intervertebral implant, the rails 118 are configured to guide the blocking plate 16 through the gap 110. The rails 118 maintain the alignment of the blocking plate 16 with the intervertebral implant as it is being affixed to the intervertebral implant.

The second section 102 of the alignment body 90 includes a flexible finger 130 that is configured to engage the groove 88 of the holding sleeve 22. As shown in FIG. 1D, the proximal end of the finger 130 defines a protrusion 134 that extends into the groove 88 when the finger 130 is engaged with the groove 88 to thereby hold the alignment mechanism 26 to the holding sleeve 22. As shown in FIG. 1D, the juncture 104 between the first section 98 and the second section 102 of the alignment body 90 forms a shoulder 138 within the channel 94 of the alignment mechanism 26. The protrusion 134 of the finger 130 and the shoulder 138 form a recess 142 therebetween and within the channel 94 that allows the alignment mechanism 26 to translate distally and proximally relative to the holding sleeve 22 without interference from the holding sleeve 22. The longitudinal length of the groove 88 determines the distance that the alignment mechanism 26 can travel. That is, the alignment mechanism 26 may travel distally along the holding sleeve 22 until the protrusion 134 of the alignment mechanism's finger 130 abuts the distal end of the groove 88 of the holding sleeve 22.

The alignment mechanism 26 may be coupled to the holding sleeve 22 by sliding the alignment mechanism 26 over the distal portion 68 of the holding sleeve 22. As the alignment mechanism 26 is being slid along the holding sleeve 22 the flexible finger 130 of the alignment mechanism 26 flexes up and rides longitudinally along an external surface of the holding sleeve 22. Once the finger 130 reaches the groove 88 defined by the proximal portion 72 of the holding sleeve 22, the finger 130 can flex back to its original position and into the groove 88 to thereby couple the alignment mechanism 26 to the holding sleeve 22. As shown in FIG. 1C, the assembly 10 may also include a spring 158 that is disposed about the distal portion 68 of the holding sleeve 22 and within the recess 142 defined by the second section 102 of the alignment mechanism 26. The spring 158 is there to resist linear motion of the alignment mechanism 26.

The driver assembly 10 may be configured to drive a fixation element 14 into an underlying structure. In one embodiment and in reference to FIGS. 5A-5D, the fixation element 14 may define a screw that includes a shaft 160 that defines longitudinally opposing proximal and distal ends 160a and 160b, respectively, and a head 164 coupled to the proximal end 160a of the shaft 160 either directly or indirectly via an unthreaded neck that is coupled between the proximal end 160a of the shaft 160 and the head 164. Helical threads 168 extend radially out from the shaft 160 at locations at and between the proximal and distal ends 160a and 160b that are configured to engage complementary threads on the inner surface of a central bore of the fixation plate of the intervertebral implant. Thus, a substantial entirety of the shaft 140 between the proximal and distal ends 160a, 160b may be threaded. As shown, however, a proximal end of the shaft 160 may be void of the threads 168.

Similarly, the fixation element 14 includes helical threads 176 that extend radially out from the head 164 at locations at and between proximal and distal ends of the head 164. The threads 176 are configured to engage the threads 68 of the holding sleeve 22 to thereby temporarily couple the fixation element 14 to the holding sleeve 22. As shown in FIG. 5D, the pitch of the threads 168 of the shaft 160 can be substantially equal to the pitch of the threads 176 of the head 164. Furthermore, the threads 168 and the threads 176 may have the same pitch direction or pitch rotation direction or handedness (i.e. right handed threads or left handed threads). That is the threads 168 and the threads 176 may extend helically around the shaft 160 and the head 164 respectively at substantially the same angle and in the same direction. Therefore, when the fixation element 14 is driven into an underlying structure, the fixation element 14 disengages from the holding sleeve 22 at the same rate that it engages the underlying structure. Though it should be understood that the pitch could be made to be different between the threads 168 of the shaft 160 and the threads 176 of the head 164 to achieve different ratios of linear motion into the underlying structure as compared to the disengagement from the holding sleeve 22. For instance the fixation element 14 can disengage from the holding sleeve 22 at a rate that is faster or slower than the rate at which the fixation element 14 engages the underlying structure. Furthermore, the fixation element 14 may have a conical threads 176 on the head 164, with the internal threads 68 of the holding sleeve 22 matching the greatest threaded diameter of the threads 176.

Figure 5A:
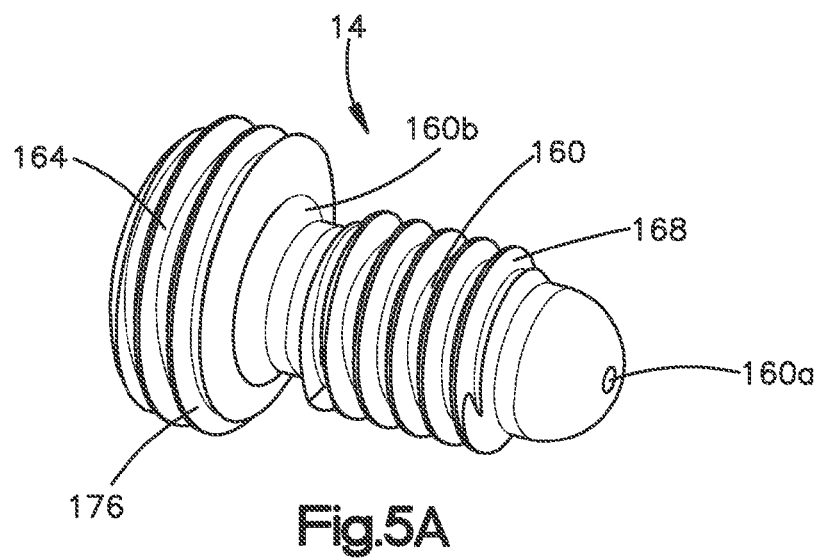
FIG. 5A is a perspective view of the fixation element shown in FIG. 1A, the fixation element having a threaded head and a threaded shaft.
Figure 5B:
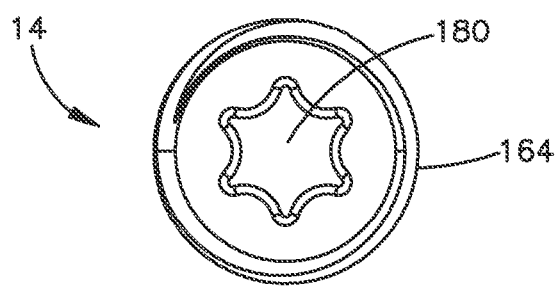
FIG. 5B is a top plan view of the fixation element shown in FIG. 5A.
Figure 5D:
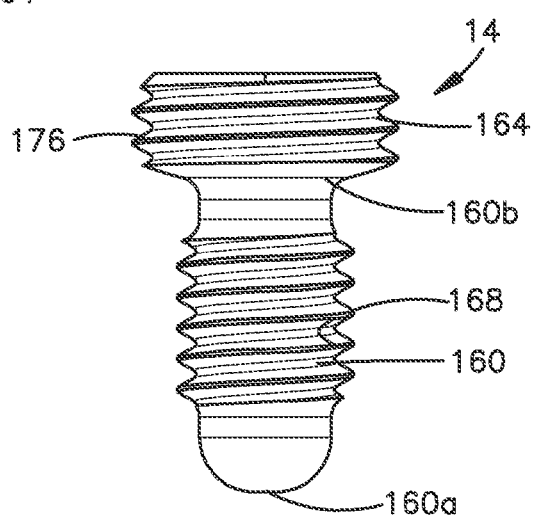
FIG. 5D is a side elevation view of the fixation element shown in FIG. 5A.
Figure 5C:
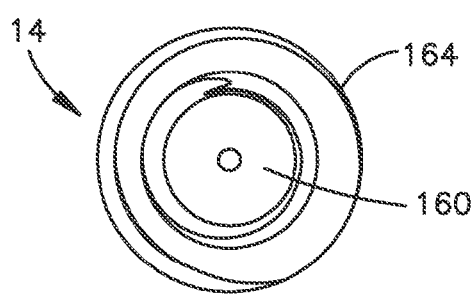
FIG. 5C is a bottom plan view of the fixation element shown in FIG. 5A.

As shown in FIG. 5B, a top surface of the head 164 of the fixation element 14 defines a coupling 180 that is configured to mate with the coupling 42 of the driver 18. As shown, the coupling 180 can be shaped as a recessed star, or can alternatively be in the shape of a recessed cruciform, a recessed hex, or any alternative shape as desired.

The fixation element 14 may be configured to affix a variety of devices to an underlying structure. For example, the fixation element 14 may be configured to affix the blocking plate 16 shown in FIGS. 6A-6E to underlying structure configured as an intervertebral implant 204 as shown in FIG. 7. The intervertebral implant 204 can be constructed as disclosed in U.S. patent application Ser. No. 12/761,101 filed Apr. 15, 2010, the contents of which are incorporated herein by reference in their entirety, or can be alternatively constructed as desired. Referring to FIG. 7, the intervertebral implant 204 includes a fixation plate 208 that is coupled to a spacer 212. As shown, one or more fixation members 216 may be utilized to securely anchor the intervertebral implant 204 within an intervertebral space between adjacent vertebral bodies. Unless otherwise indicated, the intervertebral implant 204 and its components can be manufactured from any suitable biocompatible material known in the art including but not limited to titanium, titanium alloy such as (TAN), stainless steel, reinforced plastics, allograft bone, and the like.

The fixation plate 208 is defined by a generally C-shaped body 220 that defines an anterior end 220a and laterally opposed arms 220d extending posteriorly from opposite sides of the anterior end 220a in a generally perpendicular direction from the anterior end 220a. The body 220 further defines opposed upper and lower sides 220b, 220c. The anterior, upper, lower, and arms 220a, 220b, 220c, and 220d define the general shape of a cradle that includes an internal channel that is configured to receive the spacer 212, such that the arms can at least partially surround and engage and support the spacer 212.

The fixation plate 208 may define a pair of apertures 228 that extend into the anterior end 220a, and are configured to receive the alignment members 114 of the driver assembly 10. The apertures 228 may be D-shaped, circular or any other desired shape capable of receiving the alignment members 114 so as to operatively align the fixation plate with the driver assembly 10, such that the driver assembly 10 is configured to drive the fixation elements 14 into a desired target location. For instance, the target location can be in the form of a bore 232 that extends into the anterior end 220a of the fixation plate 208, and can further extend through the body 220. The bore 232 can be centrally disposed between the arms 220d. The bore 232 is defined by an inner surface 232a of the body 220 that defines threads 236 that are configured to engage the complimentary threads 168 formed on the shaft 160 of the fixation element 14. The fixation plate 208 may also define a recess 240 that extends into the anterior end 220a and is configured to receive a complementary surface of the blocking plate 16.

As shown in FIG. 7, the fixation members 216 extend through the fixation plate 208 within the recess 240 and about the bore 232. The fixation members 216 can, for instance, extend through the fixation plate 208 at a trajectory that allows the members 216 to engage the vertebral bodies that define the intervertebral space in which the intervertebral implant 204 is disposed. The blocking plate 16 when affixed to the fixation plate 208, covers the proximal ends of the fixation members 216, thereby preventing the fixation members 216 from backing out or otherwise disengaging from the vertebral bodies.

Now referring to FIGS. 6A-6E, the blocking plate 16 includes a generally disc shaped body 260 with an anterior surface 260a and a posterior surface 260b. The anterior surface 260a of the body 260 may be generally planar, or may be defined to match the anterior end 220a of the fixation plate 208 when the blocking plate 16 is fully affixed to the fixation plate 208. Similarly the posterior surface 260b of the blocking plate 16 may be substantially planar, or may be defined to match the recess 240 formed in the anterior end 220a of the fixation plate 208 when the blocking plate 16 is fully affixed to the fixation plate 208. By having the posterior surface 260b match the recess 240 of the fixation plate 208 the blocking plate 16 will abut or otherwise lie flush against the recess 240. The posterior surface 260b can define a cross-section less than that of the anterior surface, though it should be appreciated that the blocking plate 16 can be alternatively shaped as desired.

Figure 6A:
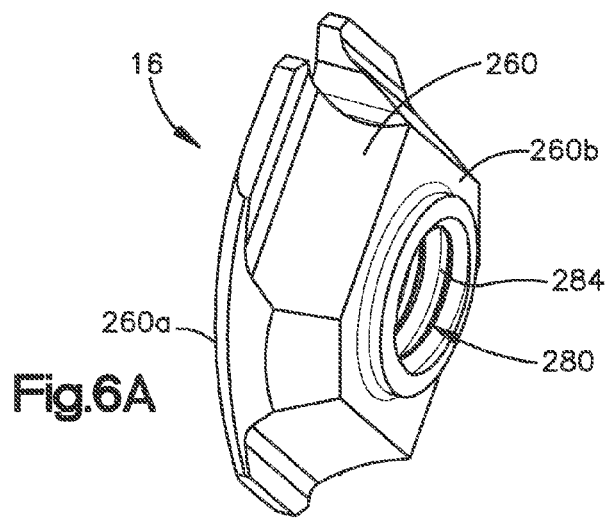
FIG. 6A is a perspective view of the blocking plate shown in FIG. 1A.
Figures 6B, 6C:
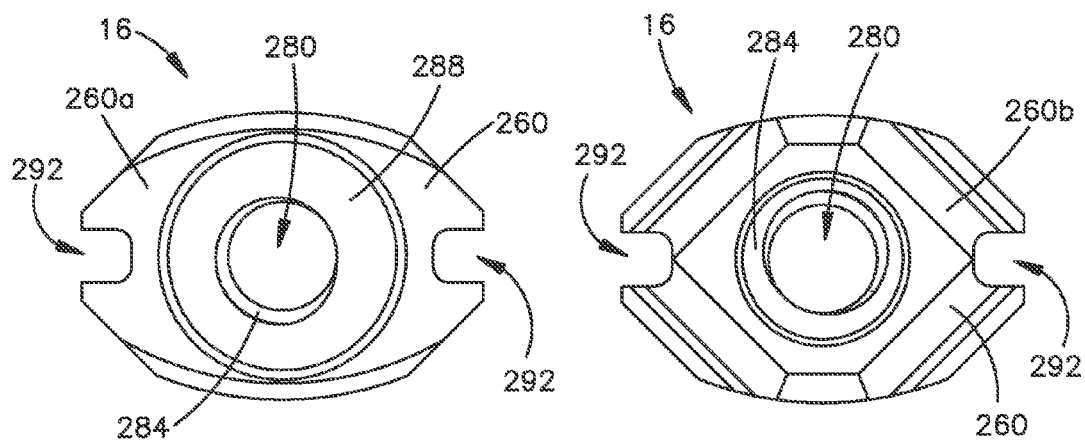
FIG. 6B is a top plan view of the blocking plate shown in FIG. 6A.
FIG. 6C is a bottom plan view of the blocking plate shown in FIG. 6A.
Figure 6D:
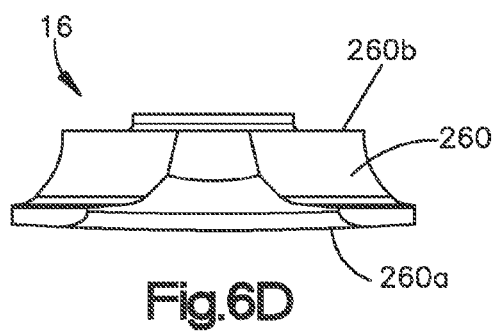
FIG. 6D is a front elevation view of the blocking plate shown in FIG. 6A.
Figure 7:
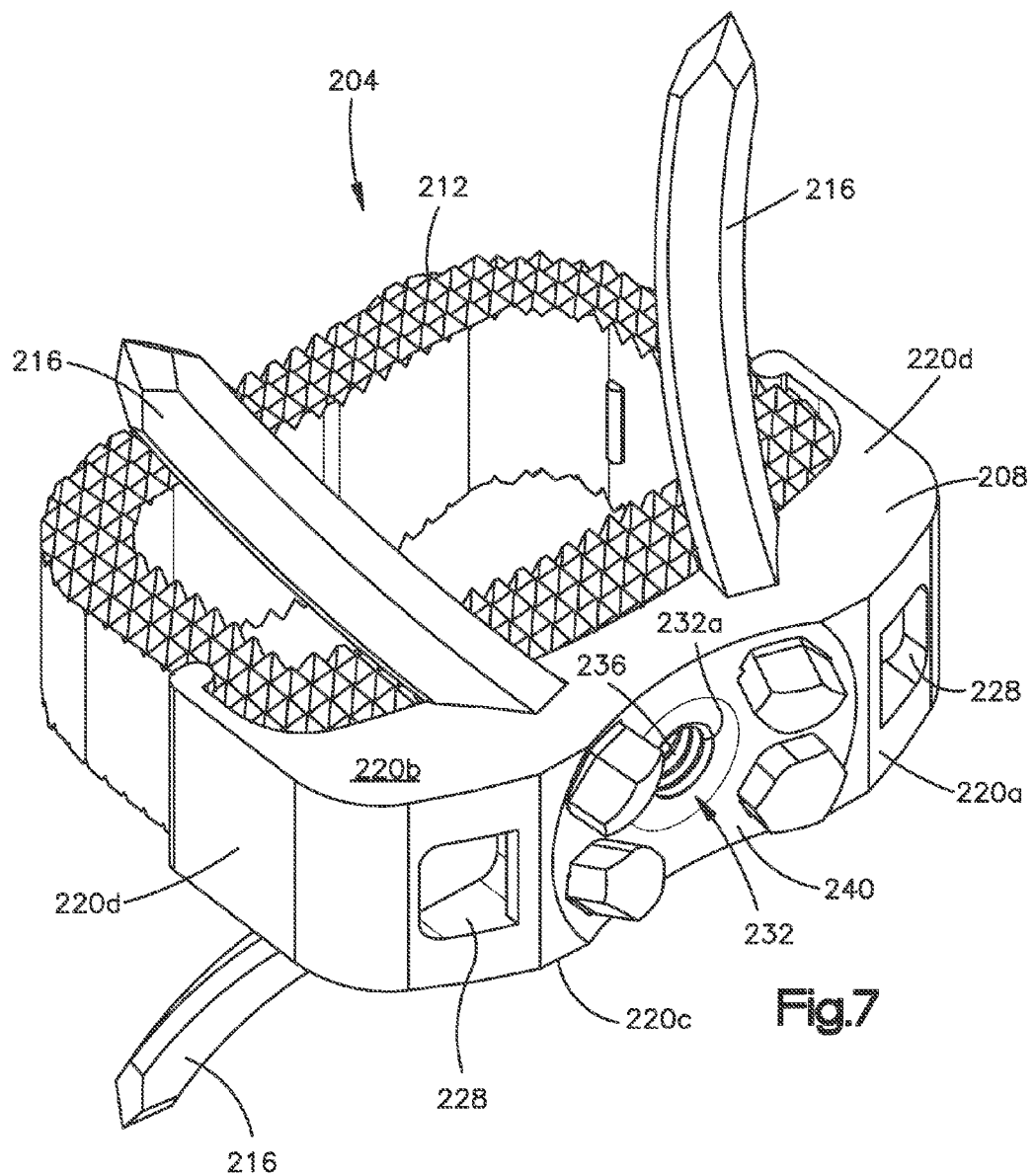
FIG. 7 is a perspective view of an intervertebral implant having a fixation plate to which the fixation element of FIGS. 5A-5D and the blocking plate of FIGS. 6A-6E are to be affixed.

As shown in FIGS. 6A-6C the blocking plate 16 further defines an aperture 280 that extends through the body 260 along a direction between the anterior surface 260a and the posterior surface 260b. The aperture 280 can by cylindrical or any suitable alternative shape, and can thus define a diameter or cross-section that is substantially equal to that of the bore 232 of the fixation plate 208. The inner surface that defines the aperture 280 may have threads 284 formed thereon, the threads 284 configured to engage complimentary threads 168 formed on the shaft 160 of the fixation element 14. The aperture 280 may further be defined by a concavity 288 that is recessed in the anterior surface 220a. The concavity 288 can be configured to receive the head 164 of the fixation element 14.

Figure 6E:
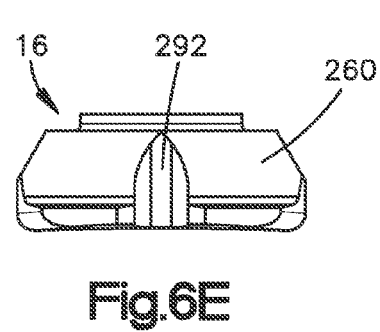
FIG. 6E is a side elevation view of the blocking plate shown in FIG. 6A.

As shown in FIGS. 6B, 6C, and 6E, the blocking plate 16 further defines a pair of grooves 292 that extend through the body 260 on either side of the aperture 280. The grooves 292 generally define C-Shaped channels that are configured to receive the rails 118 defined by the alignment mechanism 26 of the driver assembly 10. In operation as the fixation element 14 is drawn into the holding sleeve 22, the rails 118 of the alignment mechanism 26 slide into or otherwise engage the grooves 292 of the blocking plate 16 to prevent the blocking plate from rotating, and to maintain its alignment with the fixation plate 208 of the intervertebral implant 204. In other words, the rails 118 are sized and shaped substantially equal to the grooves 292 such that interference between the rails 118 and the blocking plate 16 prevents the blocking plate from rotating or otherwise changing its orientation once the rails are disposed in the grooves.

Figure 8A:
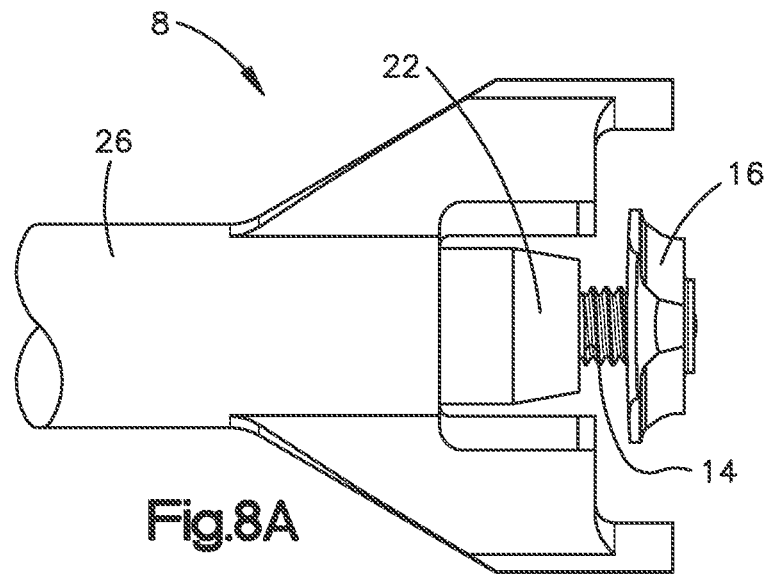
FIG. 8A is a top plan view of a portion of the fixation assembly illustrated in FIG. 1A, showing the driver engaging the head of the fixation element.
Figure 8B:
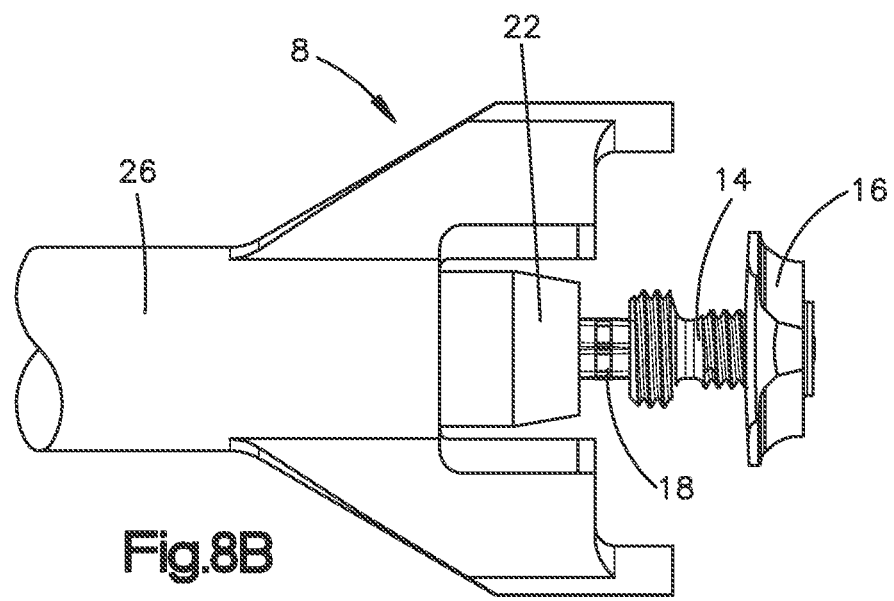
FIG. 8B is a top plan view of a portion of the fixation assembly illustrated in FIG. 8A, showing the driver retracted within the holding sleeve, and the head of the fixation element temporarily coupled to the holding sleeve.

In reference to FIGS. 8A-8G, the driver assembly 10 may temporarily hold, align, and subsequently affix the fixation element 14 and the blocking plate 16 to an underlying structure such as the fixation plate 208 of the intervertebral implant 204. As shown in FIG. 8A, the blocking plate 16 may be threaded onto the shaft 160 of the fixation element 14 before the fixation element 14 is attached to the driver 18 of the driver assembly 10. In particular, after the blocking plate 16 is attached to the fixation element 14, the coupling 42 of the driver 18 may engage the coupling 180 of the fixation element 14. By rotating the driver 18 relative to the holding sleeve 22, the fixation element 14 may be drawn into the fixation element coupler 66 of the holding sleeve 22 such that the threads 176 defined on the head 164 of the fixation element 14 engage the threads 68 defined in the channel 64 of the holding sleeve 22, as shown in FIG. 8B. This prevents the fixation element 14 and the attached blocking plate 16 from falling or being pushed off of the driver assembly 10 during the procedure. The fixation element 14 may be coupled to the holding sleeve 22 while the alignment mechanism 26 is drawn back or while it is past the distal end of the holding sleeve 22.

Once the fixation element 14 is retained by the holding sleeve 22, the alignment mechanism 26 may be translated forward as shown in FIG. 8C. The spring 158 on the interface between the alignment mechanism 26 and the holding sleeve 22 can push the alignment mechanism 26 distally such that the rails 118 of the alignment mechanism 26 slide into the grooves 292 of the blocking plate 16, thereby aligning the blocking plate 16 in a desired orientation for attachment to the fixation plate 208.

As shown in FIGS. 8D and 8E, the driver assembly 10 may then be aligned with the fixation plate 208 such that the alignment members 114 of the alignment mechanism 26 are engaged with the apertures 228 that extend through the fixation plate 208, thereby ensuring that the fixation element 14 and the blocking plate 16 are likewise aligned with the central bore 232 of the fixation plate 208.

As shown in FIG. 8F, once the assembly 8 is properly aligned to the fixation plate 208 the driver 18 is rotated. As the driver 18 is rotated, the threads 168 defined on the shaft 160 of the fixation element 14 engage the threads 236 defined by the bore 232 of the fixation plate 208. At the same time, the threads 176 defined by the head 164 of the fixation element 14 disengage from the threads 68 defined by the channel 64 of the holding sleeve 22. In the illustrated embodiment, the fixation element 14 engages the fixation plate 208 at the same rate as it disengages from the holding sleeve 22. As shown in FIG. 8F, the threads 176 defined by the head 164 of the fixation element 14 become fully disengaged from the threads 68 defined by the channel 64 of the holding sleeve 22 before the fixation element 14 becomes fully seated within the fixation plate 208. When the fixation element 14 and the blocking plate 16 have been fully seated, the driver assembly 10 may be removed from the patient with no further disengagement step, as shown in FIG. 8G.

In another embodiment and in reference to FIGS. 9A-9E, the fixation assembly may include a driver assembly 310 that has a driver 318 and a holding sleeve 322 that is disposed about the driver 318. The driver assembly 310 can further include an alignment mechanism 326 that is integrally formed with the holding sleeve 322. That is, the holding sleeve 322 and the alignment mechanism 326 may be formed as a single unit. The alignment mechanism 326 is configured to engage the underlying structure to which the fixation element 14 is to be affixed, so as to align the fixation element 14 as it is being driven by the driver 318.

As shown in FIG. 9B, the driver 318 is similar to the driver 18 shown in FIG. 2. Therefore, the driver 318 is configured to couple to the holding sleeve 322 and is configured to drive the fixation element 14 so as to cause the fixation element 14 to disengage from the holding sleeve 322 while simultaneously engaging the underlying structure to which it is to be affixed. As shown, the driver 318 includes a driver body 334, a coupling 342 that extends distally from the distal end of the driver body 334, and an engagement member 346 that extends proximally from the proximal end of the driver body 334. The coupling 342 of the driver 318 is configured to mate with a complimentary coupling of the fixation element 14. Once the coupling 42 of the driver 18 has mated with the fixation element 14, the driver 18 is configured to receive a torsional force or torque, and impart the torsional force or torque to the fixation element 14. The engagement member 346 is configured to be received by or otherwise attach to a complementary engagement member of a handle. Therefore, when the driver assembly 310 is to be used, an individual may attach the handle to the driver 318 by attaching the engagement member of the handle to the engagement member 346 of the driver 318.

As shown in FIGS. 9C and 9D, the holding sleeve 322 is elongate in the longitudinal direction L and is configured to receive the driver 318 such that either or both of the driver 318 or the holding sleeve 322 can translate in the longitudinal L direction relative to the other. As shown in FIG. 9C, the holding sleeve 322 includes a holding sleeve body 360 and a channel 364 that extends through the holding sleeve body 360 in the longitudinal direction L. The distal end of the holding sleeve body 360 defines a fixation element coupler 366 that is configured to temporarily hold a fixation element. In the illustrated embodiment, the fixation element coupler 366 includes internal threads 368 defined within the distal end of the channel 364. The internal threads 368 are configured to engage threads of the fixation element 14 to thereby securely hold the fixation element 14 to the holding sleeve 322. Similar to the embodiment shown in FIGS. 2 and 3A, the proximal end of the channel 364 defines a coupling feature such as internal threads 372 that are configured to be engaged by threads defined by the driver 318 so as to couple the holding sleeve 322 to the driver 318. Therefore, the driver 318 and the holding sleeve 322 are coupled together in a manner that is similar to the coupling of the driver 18 and the holding sleeve 22 shown in FIGS. 2 and 3A.

As shown in FIGS. 9C and 9D, the alignment mechanism 326 extends from and is integral with a distal portion of the holding sleeve 322. As shown, the alignment mechanism 326 includes a pair of struts 406 that each have a strut body 409 that extends laterally out from the holding sleeve body 360. As shown, the struts 406, also extend distally past the distal end of the holding sleeve body 360. The struts 406 are separated along a lateral direction that is substantially perpendicular with respect to the longitudinal direction, such that a gap 410 is defined between the two struts 406 adjacent a distal opening of the channel 364. As shown, each strut 106 includes an alignment member 414 that extends distally from the strut body 409. In the illustrated embodiment, the alignment members 414 are pegs or cylindrical rods, however, it should be understood that the alignment members 414 may define any shape as desired. The alignment members 414 are configured to engage the underlying structure to which the fixation element 14 is to be affixed so as to align the driver assembly 310 as well as the fixation element 14 to the underlying structure when the fixation element 14 is to be affixed to the underlying structure.

As shown in FIGS. 9C-9D, the alignment mechanism 326 can further include a rail 418 that extends out from at least one of the strut bodies 409 and into the gap 410. As shown, the two rails 418 extend parallel to each other in the longitudinal direction L, and are disposed opposite to each other within the gap 410. The rails 418, and thus the alignment mechanism 26, are configured to engage the blocking plate 16 as the fixation element 14 is temporarily coupled to the holding sleeve 322. As the fixation element 14 is advanced into an intervertebral implant, the rails 418 are configured to guide the blocking plate 16 through the gap 410. The rails 418 maintain the alignment of the blocking plate 16 with the intervertebral implant as it is being affixed to the intervertebral implant.

As best shown in FIG. 9D, the rails 418 taper as they extend distally. More particularly, the rails 418 taper to a distal point 420. The distal point 420 of each rail 418 allows the rails 418 to more easily engage the grooves 292 of the blocking plate 16.

In operation and in reference to FIG. 9E, the driver assembly 310 may be aligned with the fixation plate 208 such that the alignment members 414 of the alignment mechanism 326 are engaged with the apertures 228 that extend through the fixation plate 208, thereby ensuring that the fixation element 14 and the blocking plate 16 are likewise aligned with the central bore 232 of the fixation plate 208.

As shown in FIG. 9E, once the assembly 310 is properly aligned to the fixation plate 208 the driver 318 is rotated. As the driver 318 is rotated, the threads 168 defined on the shaft 160 of the fixation element 14 engage the threads 236 defined by the bore 232 of the fixation plate 208. At the same time, the threads 176 defined by the head 164 of the fixation element 14 disengage from the threads 368 defined by the channel 364 of the holding sleeve 322. In the illustrated embodiment, the fixation element 14 engages the fixation plate 208 at the same rate as it disengages from the holding sleeve 322. As shown in FIG. 9E, the threads 176 defined by the head 164 of the fixation element 14 become fully disengaged from the threads 368 defined by the channel 364 of the holding sleeve 322 before the fixation element 14 becomes fully seated within the fixation plate 208. When the fixation element 14 and the blocking plate 16 have been fully seated, the driver assembly 310 may be removed from the patient with no further disengagement step.

In another embodiment and in reference to FIGS. 10A and 10B, it is recognized that the driver assembly may be configured to temporarily attach to a fixation element using a thin threaded rod that engages internal threads defined in a head of the fixation element. For example, as shown in FIGS. 10A and 10B, a driver assembly 510 includes a driver 518, a holding rod 522, and an alignment mechanism 526. The driver 518 includes a driver body 530 and a channel 534 that extends through the driver body 530. The driver further includes a coupling 538 that extends distally from a distal end of the driver body 530. The channel 534 extends through both the body 530 and the coupling 538. The channel 534 is configured to receive the holding rod 522. The coupling 538 is configured to engage the head of a fixation element that is configured to be affixed to an underlying structure.

As shown in FIG. 10B, the driver 518 further includes a first protrusion 542 that extends radially out from the body 530 and a second protrusion 546 that extends radially out from the body 530 at a location proximal of the first protrusion 542. The first protrusion 542 includes external threads 548 that are configured to engage threads defined by the alignment mechanism 526. To connect the driver 518 to the alignment mechanism 526, the alignment mechanism 526 is threaded over the first protrusion 542. Once the alignment mechanism 526 and the driver 518 are properly coupled, the driver 518 will be limited in its forward motion by the second protrusion 546.

As shown in FIG. 10A, the holding rod 522 is configured to translate through the channel 534 of the driver 518 and temporarily couple to the fixation element. As shown in FIG. 10B, the holding rod 522 includes a holding rod body 550 and a fixation element coupler 554 that that extends distally from a distal end of the rod body 550. As shown, the fixation element coupler 554 includes external threads 558 that are configured to engage internal threads defined within a head of the fixation element.

In operation the holding rod 522 is threaded into the head of the fixation element 14. The alignment mechanism 526 is then aligned adjacent to a fixation plate of an intervertebral implant such that the alignment mechanism 526 engages the fixation plate. The driver 518 may then drive the fixation element into the fixation plate. Once the fixation element has been properly placed, the holding rod 522 may be unthreaded from the head of the fixation element. The driver assembly 510 may then be removed from the patient.

In another embodiment and in reference to FIGS. 11A and 11B, a driver assembly 610 may include a driver 618, and an alignment mechanism 626 that comprises a two-part tube 622 that is coupled to the driver 618 and an alignment attachment 628. The driver 618 includes a driver body 630, a coupling 634 that extends distally from the driver body 630. The driver 618 further includes an indentation 636 formed in the driver body 630 proximate to the mating feature 634.

The two part tube 622 of the alignment mechanism 626 includes a first part 642 and a separate second part 646. The first part 642 attaches to the indentation 636 defined by the driver body 630 allowing it to rotate freely relative to the driver 618. The first part 642 includes a leaf spring 650 and tabs 653 that are configured to align a blocking plate. Proximal to the tabs 653 and the leaf spring 650, the first part 642 includes threads 658. The second part 646 is threaded onto the threads 658 of the first part 642, confining the leaf spring 650 and tabs 653. The alignment attachment 628 is attached to the second part 646 and is configured to align the assembly 610 to the fixation plate. The alignment attachment 628 includes a key that allows it to slide on to the second part 646 of the tube 622 along a groove, rotate a half circle, and then follow a second groove back. A spring captive on the outside of the second part 646 provides resistive force so that driver 618 does not move relative to the alignment attachment 626.

It should be appreciated that a screw fixation kit can be provided having components from one or more embodiments described herein. For instance, the screw fixation kit can include a driver assembly, and at least one fixation element. The kit can further include a blocking plate that is configured to be affixed to an intervertebral implant. The kit can further include the intervertebral implant that the blocking plate is affixed.

Although various embodiments have been described in detail, it should be understood that various changes, substitutions, and alterations can be made herein without departing from the spirit and scope of the invention, for instance as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, composition of matter, means, methods, or steps, presently existing or later to be developed that perform substantially the same function or achieve substantially the same result as the corresponding embodiments described herein may be utilized. For example, alternative fixation elements may be used, such as a nail or a pin, that may be held captive for impaction. In such a case the fixation element coupler of the holding sleeve may be a cylinder with only a shallow bore for the head of the fixation e element, more suitable for impaction rather than a hollow tube.

What is claimed is:

1. An assembly for providing fixation to an implant having a threaded bore, comprising:
    a fixation element comprising a head with an external first thread and a shaft with a second thread configured to mate with the threaded bore of the implant; and
    a driver configured to drive the fixation element into the threaded bore of the implant;
    a holding sleeve comprising an internal channel configured to receive the driver, the holding sleeve further comprising a fixation element coupler configured to temporarily hold the fixation element, the fixation element coupler comprising an internal thread located at a distal end of the holding sleeve that mates with the first thread of the head of the fixation element;
    wherein at least one of the driver and the fixation element coupler is translatable relative to the other; and
    an alignment mechanism having at least one alignment member configured to mate with an alignment feature of the implant to align the fixation element with the threaded bore of the implant.

2. The assembly of claim 1, wherein the external first thread and second thread have the same thread pitch.

3. The assembly of claim 1, wherein the external first thread and the second thread are both right handed threads.

4. The assembly of claim 1, further comprising:
    a blocking plate, the blocking plate having a body, and defining an aperture that extends through the body, the aperture sized and configured so that that the fixation element can pass through the aperture without having a threaded connection between the fixation element and the blocking plate.

5. The assembly of claim 4, wherein the blocking plate has a pair of grooves, each groove extends through the body on respective sides of the aperture.

6. The assembly of claim 1, further comprising:
a driver assembly configured to securely hold, align, and drive the fixation element into the threaded bore of the implant.

7. The assembly of claim 6, wherein the driver assembly includes a driver having a driver body and a coupling extending from a distal end of the driver body, the coupling configured to engage a coupling defined by the head of the fixation element.

8. The assembly of claim 7, wherein the driver assembly further includes a holding sleeve having a holding sleeve body, a channel extending through the holding sleeve body, and a fixation element coupler disposed at a distal portion of the holding sleeve body, the channel configured to receive the driver, and the fixation element coupler configured to temporarily hold the fixation element.

9. The assembly of claim 1, wherein the driver assembly further includes an alignment mechanism extending from the holding sleeve, the alignment mechanism having at least one alignment member configured to engage the underlying structure to which the fixation element is to be affixed so as to align the fixation element and driver assembly with respect to the underlying structure.

10. The assembly of claim 1, further comprising:
a holding rod having a holding rod body, wherein the fixation element coupler extends distally from the holding rod body, and the driver includes a channel that extends through the driver body, the holding rod configured to translate through the channel of the driver.

11. The assembly of claim 1, wherein the alignment mechanism extends distally from the holding sleeve.

12. The assembly of claim 1, wherein the alignment mechanism is integral with the holding sleeve.

13. The assembly of claim 1, wherein the alignment mechanism includes an alignment body, and a channel that extends through the alignment body, the channel of the alignment mechanism configured to receive the holding sleeve.

14. The assembly of claim 1, wherein the alignment mechanism includes a two part tube, and an alignment attachment, the two part tube including a first part that defines tabs configured to align a blocking plate.

15. The assembly of claim 4, wherein the blocking plate has a groove that extends through the body, the groove is configured to engage the alignment mechanism so as to prevent the blocking plate from rotating, and to maintain alignment of the blocking plate with the underlying implant.

16. The assembly of claim 1, wherein the alignment mechanism further includes a pair of struts, each strut having a strut body that extends laterally out from the holding sleeve, the struts are separated such that a gap is defined between the struts adjacent a distal opening of the channel of the holding sleeve.

17. The assembly of claim 16, wherein an alignment member extends distally from each strut body.

18. The assembly of claim 1, wherein the alignment mechanism includes a mating member configured to engage a blocking plate of the implant.

19. The assembly of claim 18, wherein the mating member includes a rail that extends out from at least one of the strut bodies and into the gap.

20. The assembly of claim 19, wherein the alignment mechanism includes a pair of mating members, each mating member including a rail that extends from a respective strut body and into the gap.

* * * * *